United States Patent

Namerikawa et al.

[11] Patent Number: 5,877,411
[45] Date of Patent: Mar. 2, 1999

[54] FLUID SENSOR

[75] Inventors: Masahiko Namerikawa, Kounomiya Inazawa; Kazuyoshi Shibata, Nagoya; Yukihisa Takeuchi, Nishikamo-gun; Shigeki Nakao, Nagoya, all of Japan

[73] Assignee: NGK Insulators, Ltd., Japan

[21] Appl. No.: 857,337

[22] Filed: May 16, 1997

[30] Foreign Application Priority Data

May 22, 1996 [JP] Japan ................................. 8-127498
Oct. 18, 1996 [JP] Japan ................................. 8-276510

[51] Int. Cl.$^6$ .............. G01L 9/04; H01L 41/10; G01N 29/04
[52] U.S. Cl. .............. 73/64.53; 73/61.49; 73/54.41; 73/592; 73/24.01; 310/313 R; 310/337
[58] Field of Search ................. 73/64.53, 61.49, 73/64.42, 61.73, 54.41, 592, 597, 599, 721, 727; 310/311, 313 R, 330, 324, 337

[56] References Cited

U.S. PATENT DOCUMENTS

| | | | |
|---|---|---|---|
| 3,507,145 | 4/1970 | Loh | 73/23 |
| 3,805,592 | 4/1974 | Miller et al. | 73/32 |
| 4,193,010 | 3/1980 | Kompanek | 310/330 |
| 4,312,228 | 1/1982 | Wohltjen | 73/597 |
| 4,361,026 | 11/1982 | Muller et al. | 73/23 |
| 4,565,942 | 1/1986 | Sakai et al. | 310/338 |
| 4,586,382 | 5/1986 | Sinha | 73/703 |
| 4,721,874 | 1/1988 | Emmert | 310/333 |
| 4,741,200 | 5/1988 | Hammerle | 73/54 |
| 4,966,032 | 10/1990 | Takeuchi | 73/64 |
| 4,993,266 | 2/1991 | Omura et al. | 73/720 |
| 5,176,140 | 1/1993 | Kami et al. | 128/662.03 |
| 5,189,914 | 3/1993 | White et al. | 73/599 |
| 5,212,988 | 5/1993 | White et al. | 73/599 |
| 5,283,037 | 2/1994 | Baer et al. | 422/82.01 |
| 5,334,303 | 8/1994 | Muramatsu et al. | 204/412 |
| 5,374,521 | 12/1994 | Kipling et al. | 435/6 |
| 5,485,744 | 1/1996 | Akutagawa et al. | 73/61.49 |
| 5,705,399 | 1/1998 | Larue | 436/501 |

FOREIGN PATENT DOCUMENTS

| | | |
|---|---|---|
| 0 675 355 A1 | 10/1995 | European Pat. Off. . |
| 1-311250 | 12/1989 | Japan . |
| 2-213743 | 8/1990 | Japan . |
| 3-148040 | 6/1991 | Japan . |

*Primary Examiner*—Hezron E. Williams
*Assistant Examiner*—J. David Wiggins
*Attorney, Agent, or Firm*—Parkhurst & Wendel

[57] ABSTRACT

A fluid sensor includes a base body 2 having a vibrating portion 7, a piezoelectric element 3 which is fixed onto one surface of the vibrating portion 7 and has a piezoelectric film 4 and at least a pair of electrodes 5a, 5b which are disposed in contact with the piezoelectric film 4, an electrode terminal 6 which is disposed on the surface of the base body 2 and electrically connected to the pair of electrodes 5a, 5b, a coating material 8 which is disposed on the surface of the base body 2 in the periphery of the electrode terminal 6; pressure plates 14a, 14b, and a sealing member 12 which is held between the base body 2 and the pressure plates 14a, 14b and formed so as to surround the electrode terminal 6, wherein the electrode terminal 6 is held gas-tightly and/or liquid-tightly with respect to a fluid to be measured by holding the sealing member 12 between the coating material 8 and the pressure plates 14a, 14b.

5 Claims, 26 Drawing Sheets

FIG. 16 A
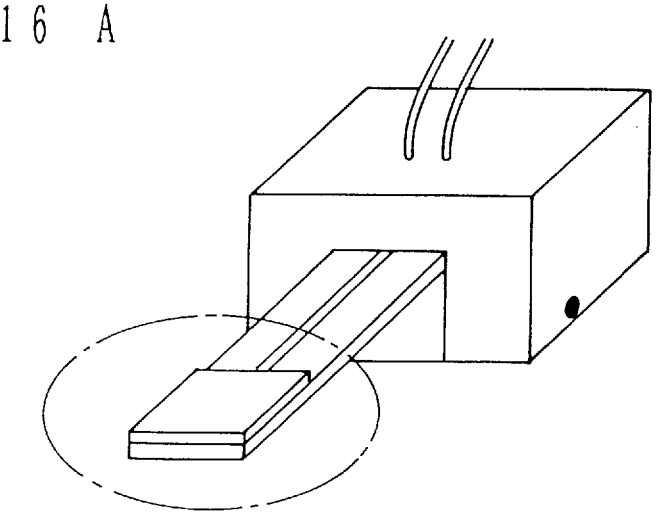
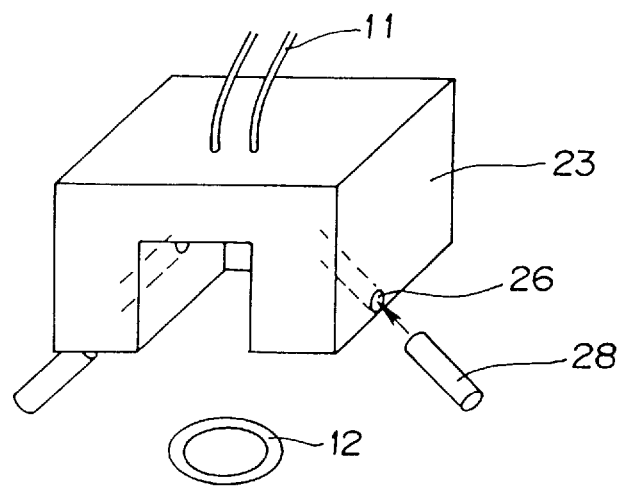
FIG. 16 B
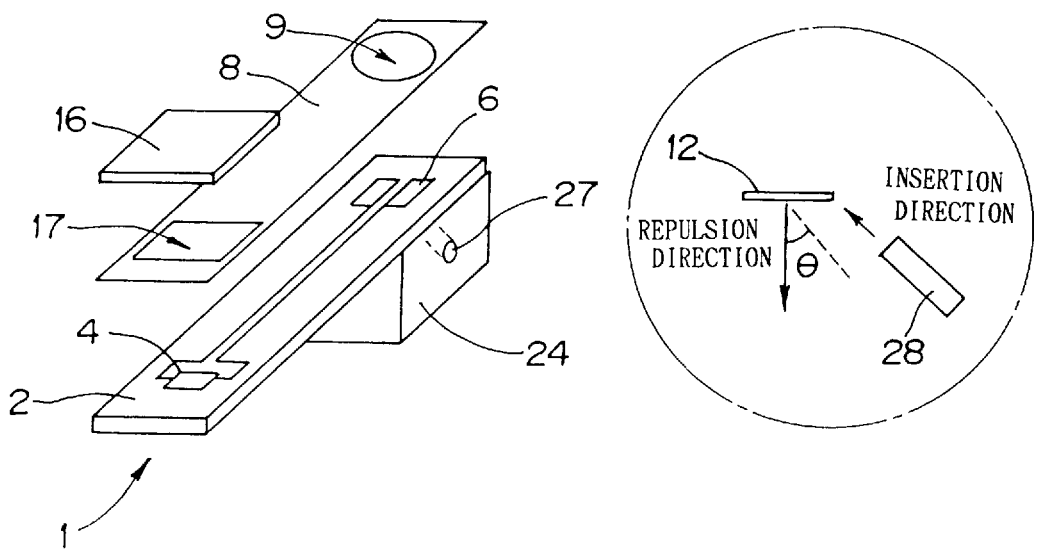
FIG. 16 C

ELASTIC MEMBER 36

FLUID SENSOR

BACKGROUND OF THE INVENTION

1. Field of the Invention

The present invention relates to a fluid sensor that actuates in a fluid, and more particularly to a fluid sensor that actuates in a corrosive fluid such as sulfuric acid, particularly in a lead storage battery or in a polar solvent tank.

2. Description of Related Art

A sensor device having a piezoelectric element or the like is used for the measurement of the viscosity of a fluid, the detection of solid particles in a fluid, the detection of vibrations, etc. For example, in the sensor device disclosed in U.S. patent application Ser. No. 08/560,658, a piezoelectric film and a vibrating portion are vibrated, and the viscosity of a fluid is measured in accordance with a change in the loss coefficient, the electric resistance, the reactance or the like of the piezoelectric film. In this example, since the piezoelectric film or the vibrating portion is in contact with the fluid, when the viscosity of the fluid is large, the vibration of the piezoelectric film and the vibrating portion become small in amplitude. On the other hand, when the viscosity of the fluid is small, the vibration of the piezoelectric film and the vibrating portion become large in amplitude. Then, when a voltage is applied to the piezoelectric film, a current corresponding to the amplitude is detected. In the case where the viscosity of the fluid correlates with the concentration of the fluid or the density of components in the fluid, the concentration or the density of the fluid can be also detected. For example, a sulfuric acid aqueous solution has a given correlation between the viscosity and the concentration, as well as a given correlation between the viscosity and the density of sulfuric acid.

Also, the detection of solid particles in the fluid is proposed in U.S. patent application Ser. No. 08/443,464 that discloses a particle sensor having a piezoelectric film. With the collision of particles in the fluid with a detecting portion having the piezoelectric film or a vibrating portion to which the detecting portion is fixed, the vibrating portion and the detecting portion vibrate, the piezoelectric film converts the vibrations into an electric signal, and a pair of electrodes between which the piezoelectric film is interposed outputs that electric signal.

In the case of measuring the viscosity of the fluid, detecting the solid particles in the fluid, and detecting the vibrations by use of the above-structured sensor device, there is required that the sensor device is disposed in the fluid with the result that an electrode terminal for extracting a signal from the sensor device that actuates in the fluid to the exterior must be held gas-tightly and/or liquid-tightly with respect to the fluid.

For the above reason, up to now, as shown in FIG. 5, a lead wire 11 is connected to an electrode terminal 6, and its connected portion is then molded with an organic resin 30 or the like so as to be sealed such that the electrode terminal is held gas-tightly and/or liquid-tightly with respect to the fluid.

However, in the above conventional method, because an adhesion of the organic resin to a ceramic material of which a base body of the sensor device is made is weak, there arises such a problem that the molding organic resin 30 or the like is caused to be readily separated from the connected portion.

SUMMARY OF THE INVENTION

The present invention has been made in view of the above problems with the prior art, and therefore an object of the present invention is to provide a fluid sensor which is capable of readily and surely holding an electrode terminal for extracting a signal from the sensor device to the exterior gas-tightly and/or liquid-tightly with respect to the fluid.

In order to achieve the above object, according to the present invention, there is provided a fluid sensor which comprises: a base body having a vibrating portion; a piezoelectric element which is fixed onto one surface of said vibrating portion and has a piezoelectric film and at least a pair of electrodes which are dispose in contact with said piezoelectric film; an electrode terminal which is disposed on the surface of said base body and electrically connected to said pair of electrodes; a coating material which is disposed on the surface of said base body in the periphery of said electrode terminal; a pressure plate; and a sealing member which is held between said base body and said presser plate and formed so as to surround said electrode terminal; wherein said electrode terminal is held gas-tightly and/or liquid-tightly with respect to a fluid to be measured by holding said sealing member between said coating material and said presser plate.

It is preferable that the fluid sensor according to the present invention further comprises a lead wire that penetrates said presser plate; and an electrode connection member disposed on a top of said lead wire, wherein said electrode connection member and said electrode terminal are in contact with each other.

It should be noted that the fluid is mainly directly to a liquid, more particularly to a high-corrosive fluid such as sulfuric acid aqueous solution used in a lead storage battery, a polar solvent such as water or a solution using the polar solvent.

BRIEF DESCRIPTION OF THE DRAWINGS

These and other objects, features and advantages of the present invention will become more fully apparent from the following detailed description taken with the accompanying drawings in which:

FIGS. 1A and 1B show an example of a fluid sensor in accordance with the present invention, in which FIG. 1A is a schematically perspective view of the fluid sensor, and FIG. 1B is a schematically exploded view of the fluid sensor;

FIGS. 3A to 3C show an example of a fluid sensor in which the periphery of a flat base body is sealed, in which FIG. 3A is a schematically perspective view of the fluid sensor, FIG. 3B is a schematically exploded view of the fluid sensor; and FIG. 3C is a schematically cross-sectional view of the fluid sensor;

FIGS. 6A and 6B show another example of a fluid sensor in accordance with the present invention, in which FIG. 6A is a schematically perspective view of the fluid sensor, and FIG. 6B is a schematically exploded view of the fluid sensor;

FIGS. 7A and 7B show another example of a fluid sensor in accordance with the present invention, in which FIG. 7A is a schematically perspective view of the fluid sensor, and FIG. 7B is a schematically exploded view of the fluid sensor;

FIGS. 8A and 8B show another example of the fluid sensor in accordance with the present invention, in which FIG. 8A is a schematically perspective view of the fluid sensor, and FIG. 8B is a schematically exploded view of the fluid sensor;

FIGS. 9A and 9B show another example of a fluid sensor in accordance with the present invention, in which FIG. 9A is a schematically perspective view of the fluid sensor, and FIG. 9B is a schematically exploded view of the fluid sensor;

FIGS. 10A and 10B show another example of a fluid sensor in accordance with the present invention, in which FIG. 10A is a schematically perspective view of the fluid sensor, and FIG. 10B is a schematically exploded view of the fluid sensor;

FIGS. 11A and 11B show another example of a fluid sensor in accordance with the present invention, in which FIG. 11A is a schematically perspective view of the fluid sensor, and FIG. 11B is a schematically exploded view of the fluid sensor;

FIGS. 12A and 12B show another example of a fluid sensor in accordance with the present invention, in which FIG. 12A is a schematically perspective view of the fluid sensor, and FIG. 12B is a schematically exploded view of the fluid sensor;

FIGS. 13A and 13B show another example of a fluid sensor in accordance with the present invention, in which FIG. 13A is a schematically perspective view of the fluid sensor, and FIG. 13B is a schematically exploded view of the fluid sensor;

FIGS. 14A and 14B show another example of a fluid sensor in accordance with the present invention, in which FIG. 14A is a schematically perspective view of the fluid sensor, and FIG. 14B is a schematically exploded view of the fluid sensor;

FIGS. 15A and 15B show another example of a fluid sensor in accordance with the present invention, in which FIG. 15A is a schematically perspective view of the fluid sensor, and FIG. 15B is a schematically exploded view of the fluid sensor;

FIGS. 16A and 16B show another example of a fluid sensor in accordance with the present invention, in which FIG. 16A is a schematically perspective view of the fluid sensor, FIG. 16B is a schematically exploded view of the fluid sensor, and FIG. 16C shows the relationship between the insertion direction and the repulsion direction;

FIGS. 17A, 17B and 17C show another example of a fluid sensor in accordance with the present invention, in which FIG. 17A is a schematically perspective view of the fluid sensor, and FIG. 17B is a schematically exploded view of the fluid sensor;

FIGS. 18A and 18B show another example of a fluid sensor in accordance with the present invention, in which FIG. 18A is a schematically perspective view of the fluid sensor, and FIG. 18B is a schematically exploded view of the fluid sensor;

FIGS. 19A 19B and 19C show another example of a fluid sensor in accordance with the present invention, in which FIG. 19A is a schematically perspective view of the fluid sensor, and FIG. 19B is a schematically exploded view of the fluid sensor;

FIGS. 20A and 20B show another example of a fluid sensor in accordance with the present invention, in which FIG. 20A is a schematically perspective view of the fluid sensor, and FIG. 20B is a schematically exploded view of the fluid sensor;

FIGS. 21A and 21B show another example of a fluid sensor in accordance with the present invention, in which FIG. 21A is a schematically perspective view of the fluid sensor, and FIG. 21B is a schematically exploded view of the fluid sensor;

FIGS. 22A and 22B show another example of a fluid sensor in accordance with the present invention, in which FIG. 22A is a schematically perspective view of the fluid sensor, and FIG. 22B is a schematically exploded view of the fluid sensor;

FIGS. 23A and 23B show another example of a fluid sensor in accordance with the present invention, in which FIG. 23A is a schematically perspective view of the fluid sensor, and FIG. 23B is a schematically exploded view of the fluid sensor;

FIGS. 24A and 24B show another example of a fluid sensor in accordance with the present invention, in which FIG. 24A is a schematically perspective view of the fluid sensor, and FIG. 24B is a schematically exploded view of the fluid sensor;

FIGS. 25A and 25B show another example of a fluid sensor in accordance with the present invention, in which FIG. 25A is a schematically perspective view of the fluid sensor, and FIG. 25B is a schematically exploded view of the fluid sensor;

FIGS. 26A and 26B show another example of a fluid sensor in accordance with the present invention, in which FIG. 26A is a schematically perspective view of the fluid sensor, and FIG. 26B is a schematically exploded view of the fluid sensor; and FIGS. 27A and 27B show another example of a fluid sensor in accordance with the present invention, in which FIG. 27A is a schematically perspective view of the fluid sensor, and FIG. 27B is a schematically exploded view of the fluid sensor.

DETAILED DESCRIPTION OF THE PREFERRED EMBODIMENTS

Now, a description will be given in more detail of preferred embodiments of the present invention with reference to the accompanying drawings.

Figure 1:
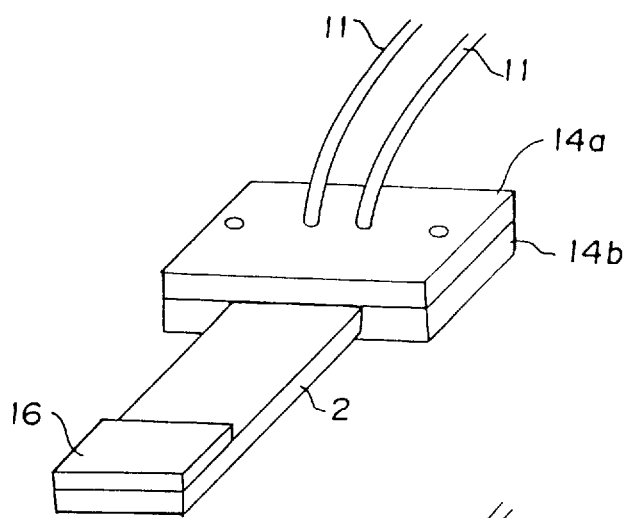
Figure 1:
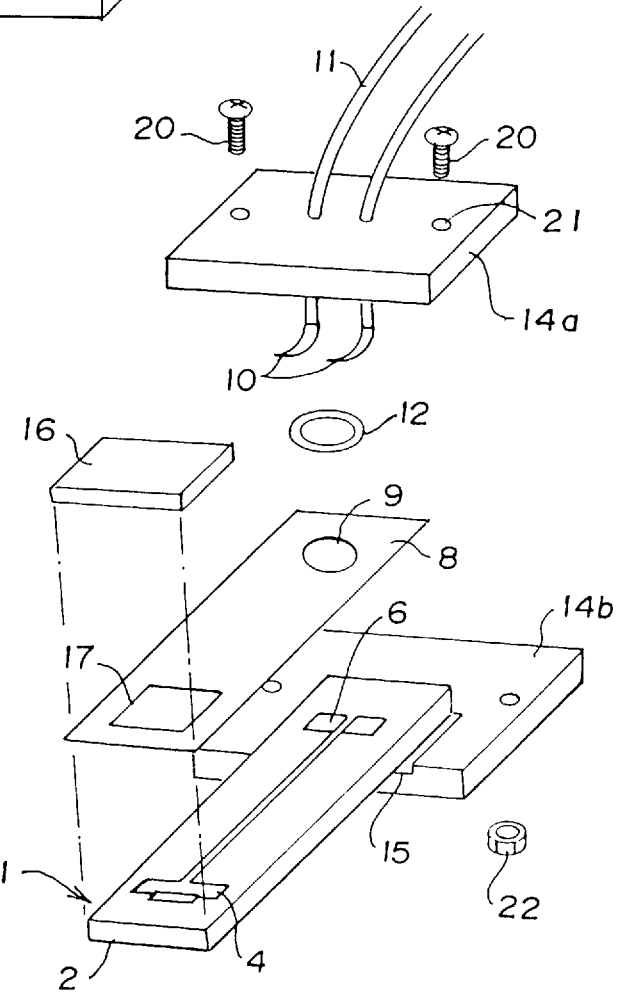
Figure 2:
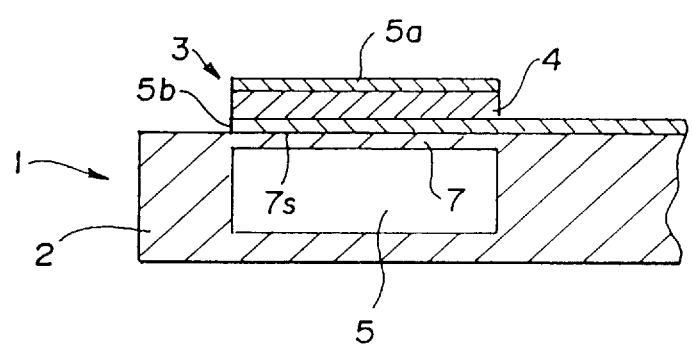
FIG. 2 is a cross-sectional view explanatorily showing an example of a sensor device.

FIGS. 1A and 1B show an example of a fluid sensor in accordance with the present invention, in which FIG. 1A is a schematically perspective view of the fluid sensor, and FIG. 1B is a schematically exploded view of the fluid sensor. FIG. 2 is a cross-sectional view explanatorily showing an example of a sensor device.

In the figures, a sensor device 1 includes a flat base body 2 having a vibrating portion 7, and a piezoelectric element 3 which is fixed onto one surface 7s of the vibrating portion 7. An inner space 5 is defined in the flat base body 2 so that the vibrating portion 7 is thinned. Although being not shown, the inner space 5 is structured such that a fluid to be measured is led to the inner space 5 through a hole or the like formed in a part of the base body 2. The piezoelectric element 3 includes a piezoelectric film 4 and a pair of electrodes 5a and 5b between which the piezoelectric film 4 is interposed. Also, an electrode terminal 6 which is electrically connected to the pair of electrodes 5a and 5b is formed on the surface of the flat base body 2.

A coating material 8 which is formed of a glass printed layer is disposed on the surface of the flat base body 2 on which the electrode terminal 6 is disposed so as to cover a peripheral portion that surrounds the electrode terminal 6. A hollow-out portion 9 where a portion corresponding to the electrode terminal 6 is hollowed out is formed on the coating material 8. It should be noted that a hollow-out portion 17 where a portion corresponding to the piezoelectric element 3 of the flat base body 2 is hollowed out is also formed on the coating material 8, and the upper portion of the hollow-out portion 17 is covered with and fixed to a cover 16 which is made of a ceramic material such as $ZrO_2$.

An O-ring 12 which is a sealing member formed so as to surround the electrode terminal 6 is held between the flat base body 2 and a presser plate 14a so as to correspond to the hollow-out portion 9 of the coating material 8. A lead wire 11 having a plate spring shaped terminal 10 at its top is held to penetrate the presser plate 14a in such a manner that it is in contact with the electrode terminal 6. Also, for accommodating a side of the flat base body 2 where no electrode terminal 6 is formed, a depression 15 is defined in the presser plate 14b.

As described above, the O-ring 12 is held between the surface of the flat base body 2 in the periphery of the electrode terminal 6 or the surface of the coating material 8 and the surfaces of the presser plates 14a, 14b, to thereby hold the electrode terminal 6 of the flat base body 2 gas-tightly and/or liquid-tightly with respect to the fluid to be measured.

A gap between the presser plate 14a and the lead wire 11 is kept in a liquid seal state in such a manner that the gap is filled with a sealing material which is liable to adhere to both the presser plate 14a and the lead wire 11, these members are fitted to each other so that the gap is made substantially zero, or these members are integrally molded.

Figure 3A:
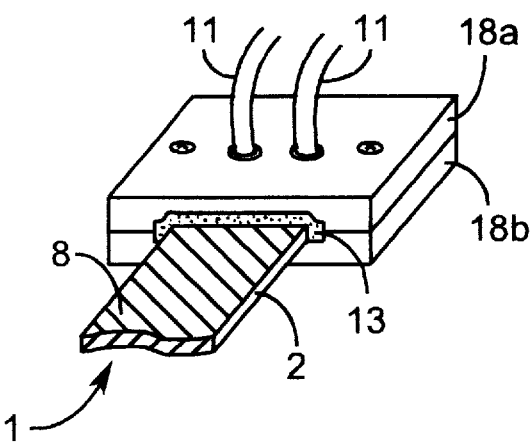
Figure 3B:
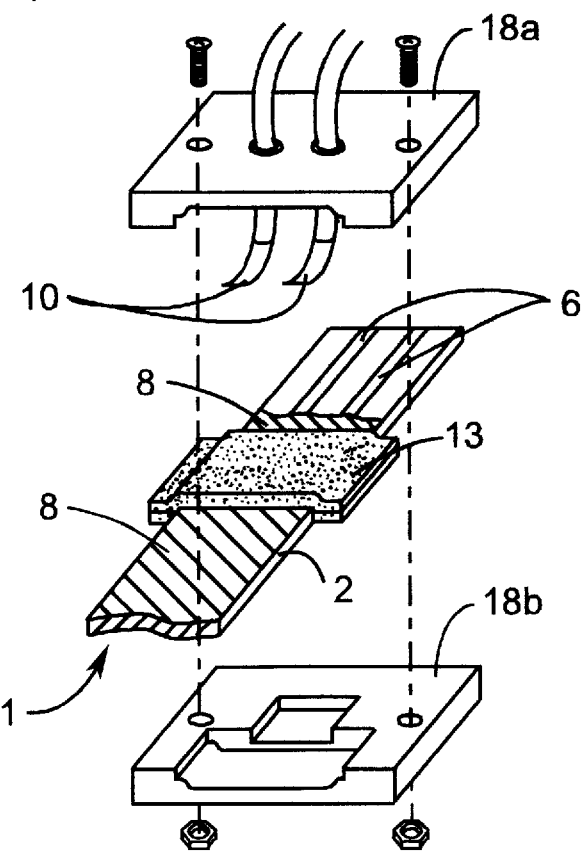
Figure 3C:
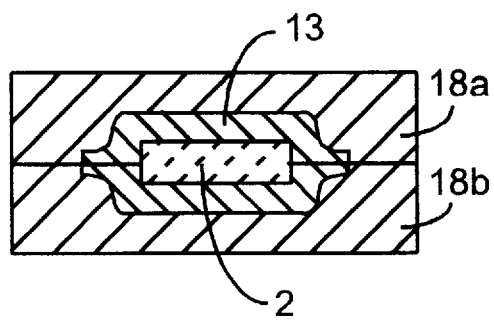
Figure 4:
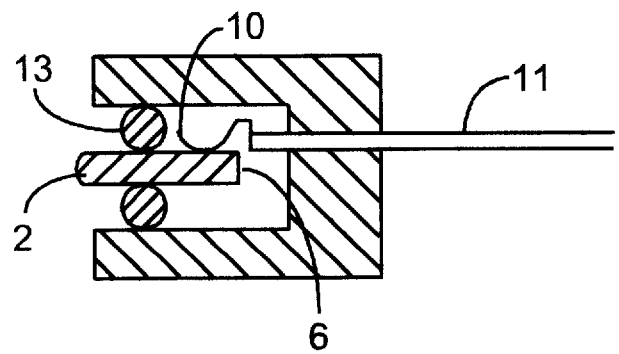
FIG. 4 is a partially cross-sectional view explanatorily showing the peripheral portion of the electrode terminal.
Figure 5:
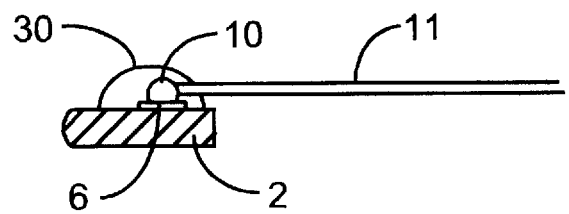
FIG. 5 is a partially cross-sectional view explanatorily showing the peripheral portion of an electrode terminal in a conventional fluid sensor.

FIGS. 3A to 3C show an example of a fluid sensor in the case where the periphery of the flat base body is sealed, in which FIG. 3A is a schematically perspective view of the fluid sensor, FIG. 3B is a schematically exploded view thereof, and FIG. 3C is a schematically cross-sectional view thereof. FIG. 4 is a partially cross-sectional view explanatorily showing the peripheral portion of the electrode terminal.

In the example shown in FIG. 3A to 3C, in order that the electrode terminal 6 existing on an end portion of the surface of the flat base body 2 is held gas-tightly and/or liquid-tightly with respect to the fluid, the periphery of the flat base body 2 is coated with a sealing member 13, and both surfaces of the sealing member 13 are fixedly held between a pair of presser plates 18a and 18b, to thereby hold the electrode terminal 6 gas and/or liquid tightly with respect to the fluid to be measured.

Even in this example, the presser plates 18a, 18b and the lead wire 11 are structured in a liquid seal state as in the above example of FIG. 2, and in addition, the peripheries of the presser plates 18a and 18b are adhered with adhesive, or the sealing member 13 is extended, whereby the electrode terminal 6 is held gas-tightly and/or liquid-tightly with respect to the fluid to be measured.

It should be noted that in this example, because there is the possibility that the reliability of sealing on the thick (step) portion of the sensor device 1 by the sealing member 13 is poor, it is important to select a material rich in flexibility as a material of the sealing member 13. Regarding this matter, the example shown in FIGS. 1A and 1B does not suffer from such a problem that the reliability of sealing is poor because of the thickness of the sensor device 1, thereby being capable of surely sealing the electrode terminal 6 gas-tightly and/or liquid-tightly with respect to the fluid.

In the fluid sensor according to the present invention, the base body 2 is preferably flat-shaped, but may be bar-shaped or pipe-shaped. Also, the material of the base body 2 is preferably ceramics, and more preferably a material mainly containing zirconia and alumina therein.

The vibrating portion 7 is preferably in the form of a plate which is suitable for vibrations, and the piezoelectric device 3 is disposed on one surface of the vibrating portion 7.

The piezoelectric device 3 includes the piezoelectric film 4 and a pair of electrodes 5a and 5b between which the piezoelectric film 4 is interposed. When a voltage is applied to the piezoelectric film 4 through the pair of electrodes 5a and 5b, dielectric polarization is developed with the result that the piezoelectric element 3 flexibly vibrates in the thickness direction of the piezoelectric film 4 and the vibrating portion 7 together with the vibrating portion 7.

The electrode connection member 10 such as a plate spring shaped terminal is disposed on a top of the lead wire 11 that penetrates the presser plate 14a, and the electrode connection member 10 and the electrode terminal 6 are in contact with each other.

The method of contacting the electric connection portion 10 with the electrode terminal 6 may be a method in which the electric connection member 10 is formed of an electrode pole or bar for press-fitting or contact bonding or the like which is made of a material which is liable to be deformed by a mechanical stress so that the electrode pole is deformed to ensure conduction by a mechanical contact, or a method in which the electric connection member 10 is formed of a flowabilitive conductive member such as a solder or an electrically conductive paste, and the conductive member is solidified to ensure conduction, other than the mechanical method using the plate spring terminal or the like as the electric connection member 10.

The coating material 8 is disposed so as to cover at least a side of the piezoelectric element 3 with respect to the electrode terminal 6 on the surface of the flat base body 2 on which the electrode terminal 6 is disposed.

The coating material 8, in the case where the electrode terminal 6 is disposed on the surface of the flat base body 2, need not always have an area equivalent to the surface of the flat base body 2 if the coating material 8 is structured so as to cover the electrode terminal 6, and the hollow-out portion 9 for the electrode terminal and the frame-shaped hollow-out portion 17 for the cover are preferably formed on both ends of the coating material 8. It should be noted that the frame-shaped hollow-out portion 17 for the cover is not always required if it is so arranged as to prevent the coating material 8 from being in direct contact with the piezoelectric element 3.

The kind of material of the coating material 8 is not particularly limited, but it is preferably made of glass, organic resin, ceramics, etc.

It should be noted that because the base body 2 is preferably made of ceramics, it is more preferable that the coating material 8 is made of glass from the viewpoint of adhesion.

In this case, it is preferable that the coating material 8 made of glass is disposed on the base body 2, then the cover 16 is located so as to cover the hollow-out portion 17, and thereafter they are melted by heating so that the coating material 8 adheres to the base body 2 as well as the cover 16. Also, in the case where the cover 16 is not disposed, it is preferable that the hollow-out portion 17 of the coating material 8 is omitted, and after a material that disappears by heating is disposed between the coating material 8 of the portion corresponding to the hollow-out portion 17 and the piezoelectric element 3, they are heated so that a space is provided between the piezoelectric element 3 and the coating material 8, and simultaneously the coating material 8 is made to adhere to the base body 2.

The sealing member 12 is preferably formed of the O-ring as shown in FIG. 1B, but it is not limited thereto, and any member which is structured to surround the electrode terminal 6 can be used as the sealing member 12 without any problem.

The O-ring 12 that forms the sealing member is held between the presser plate 14a and the coating material 8, and further held between the flat base body 2 and the presser plate 14b, as a result of which the O-ring 12 is elastically deformed by the surface of the coating material 8 and the surfaces of the presser plates 14a, 14b so that the gas is closed, thereby being capable of surely holding the lead wire 11, the electrode connection member 10 and the electrode terminal 6 gas-tightly and/or liquid-tightly with respect to the fluid to be measured.

It is preferable that the material of the sealing members 12 and 13 is a material excellent in elastic deformation.

However, there arises no problem if the material can hold the electrode connection member 10 and the electrode terminal 6 gas-tightly and/or liquid-tightly with respect to the fluid to be measured even though it is plastic-deformed.

The material of the sealing members 12 and 13 which satisfies the above conditions is, for example, a rubber material such as fluoro rubber, acrylate rubber, silicon rubber, butyl rubber, nitrile rubber, or urethane rubber, an organic resin such as soft vinyl chloride, polyester or urethan.

With the provision of only one of the presser plates 14a and 14b, the presser plate may be held between the base body 2 and the single presser plate. However, it is preferable that as shown in FIG. 1B, the presser plates 14a and 14b are disposed on both sides of the flat base body 2 to hold the flat base body 2 therebetween because seal can be more surely achieved.

In the case where the presser plates 14a and 14b are used on both sides of the flat base body 2, as shown in FIG. 1B, bolts 20 are made to penetrate holes 21 defined in the presser plates 14a and 14b, respectively, and then screwed with nuts 22, thereby being capable of holding the presser plates 14a and 14b.

As other methods, there can be used a method in which after bar-shaped bodies made of an organic resin are so arranged as to penetrate holes 21 defined in the presser plates 14a and 14b, respectively, parts protruded from the presser plates 14a and 14b are deformed by heating while a pressure is applied to the presser plates 14a and 14b, thereby holding the presser plates 14a and 14b, or a method in which the presser plates 14a and 14b are pressed by claws provided on the presser plates 14a and 14b so that those claws are entwined with each other, thereby holding both the presser plates 14a and 14b. However, if there is used a member which can firmly hold the flat base body 2 and other members, it is not particularly limited.

It is preferable that as shown in FIG. 3C, the presser plates 18a and 18b are disposed on both sides of the flat base body 2, and held by the sealing member 13 coated on the periphery of the flat base body 2.

In this case, it is preferable that the presser plates 18a and 18b is of a shape which is liable to be integrated with the flat base body 2 coated with the sealing member 13, and which copes with the elastic change of the sealing member 13.

The material of the presser plate 14 is not particularly limited, but preferably made of ceramics, glass, organic resin or the like. The material of the presser plate 14 is more preferably made of vinyl chloride, polyester, ABS, acrylic or polypropylene and most preferably made of the same material as the coating material of a coated lead wire, from the viewpoint of the costs.

The means for holding the flat base body is not limited to a plate body such as the above presser plate, for example, the flat base body may be held between two kinds of support members 23 and 24 one of which is fitted into the other as shown in FIGS. 6A and 6B (In this specification, these support members are called "standard type" in comparison with "box type" which will be described later.).

The flat base body 2 is set in a recess 25 of one support member 23 and held by another support member 24, and then shaft bodies 28 are made to penetrate holes 26 and 27 defined in these two different members 23 and 24 in such a manner that these two different support members 24 and 24 are fixed to each other in a state where the flat base body 2 is held between those support members 23 and 24.

With the above structure, the shapes of parts are simplified, thereby being capable of reducing the number of members, simplifying the process and improving in corrosion resistance.

Figure 7:
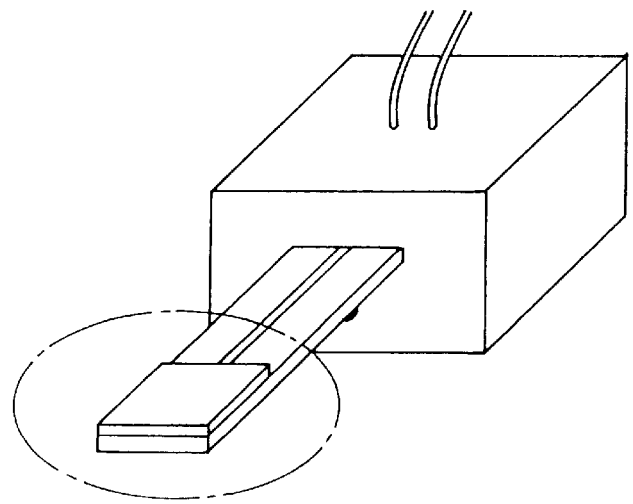
Figure 7:
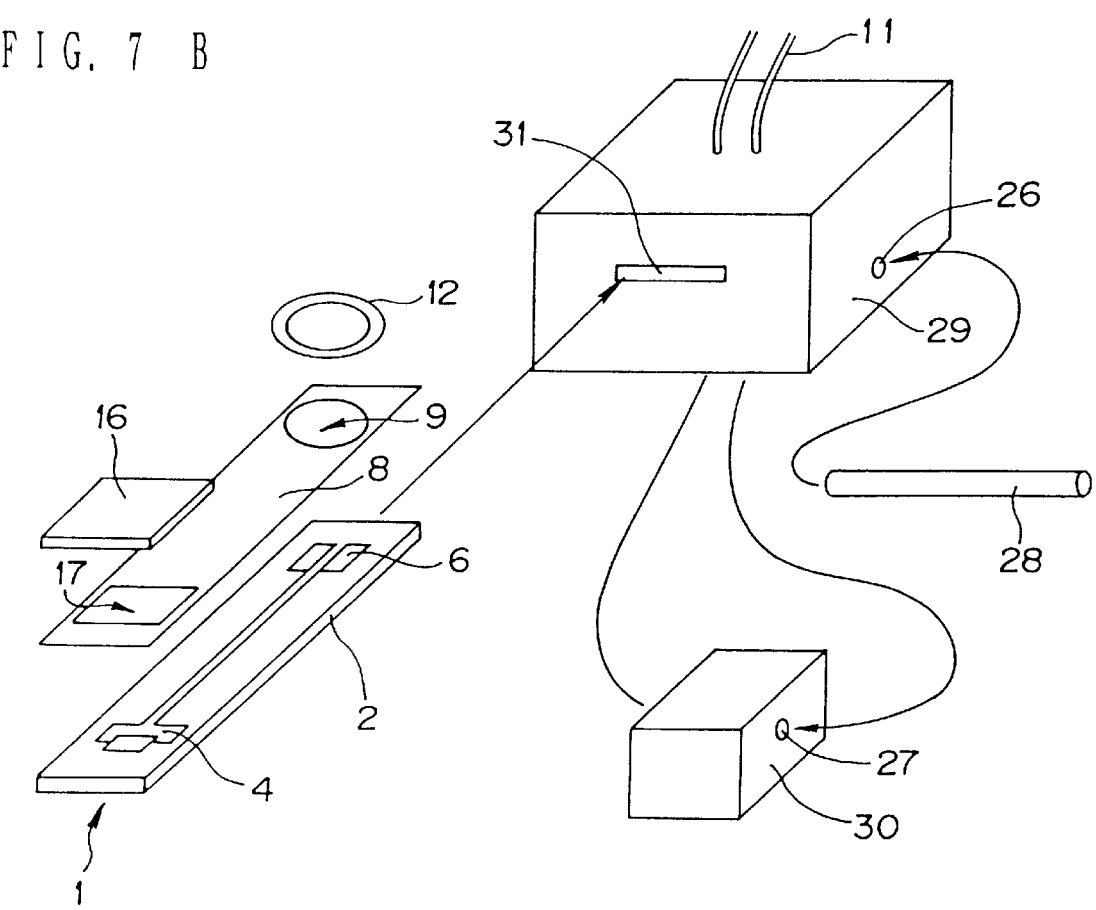
Figure 8:
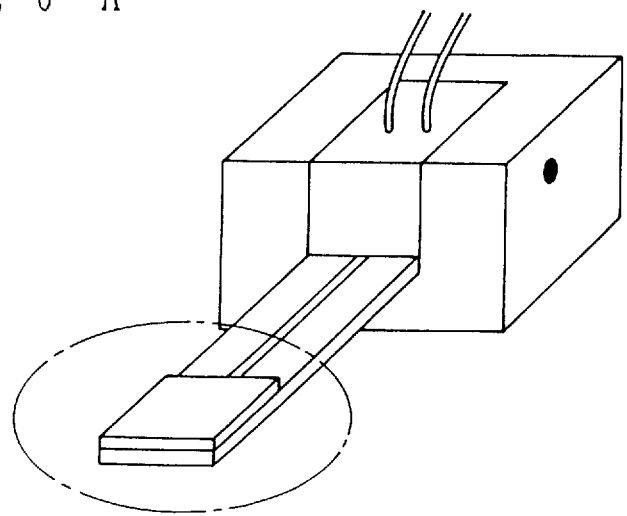
Figure 8:
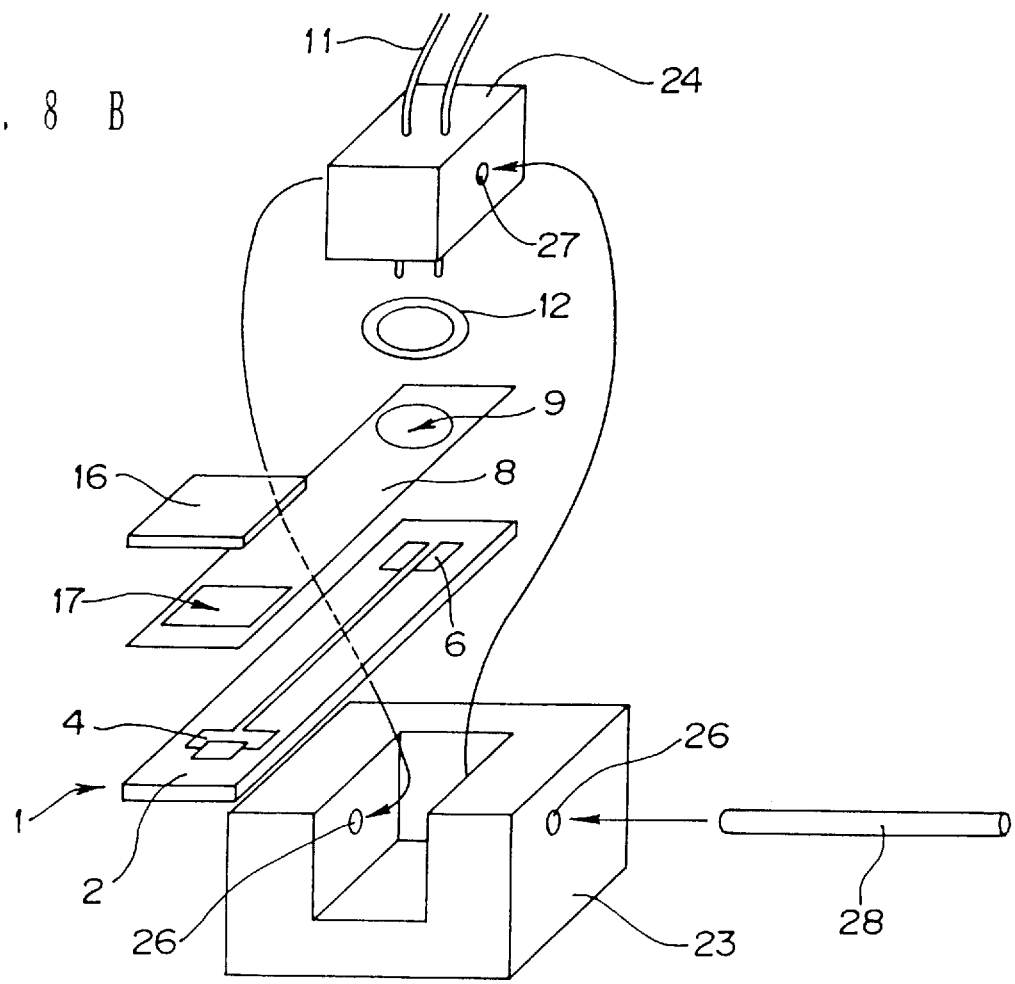
Figure 9:
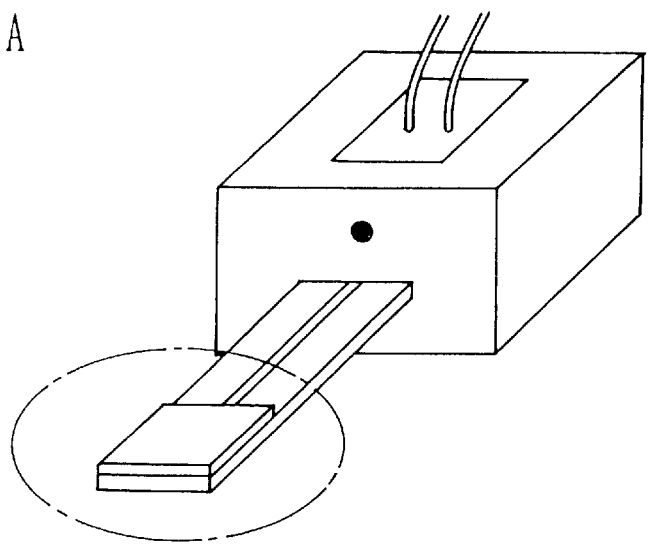
Figure 9:
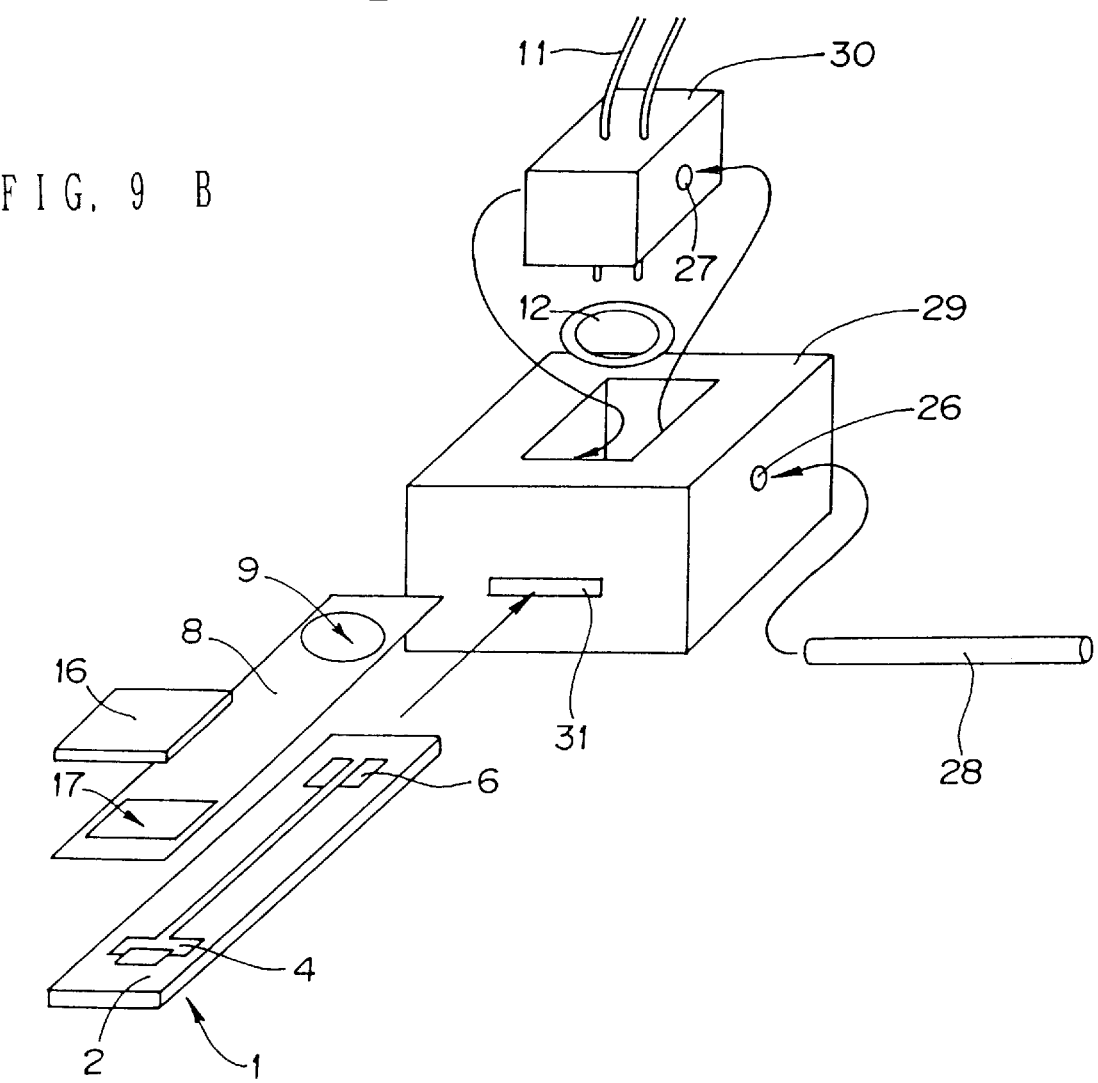

As the shape of the support members, box-type members 29 and 30 shown in FIGS. 7A and 7B may be used, an opening portion 31 into which the flat base body 2 is inserted may be in the member 29. Also, as shown in FIGS. 8A, 8B and 9A, 9B, the support members 23 and 24, 24 and 29 may turn upside down, respectively.

The sectional shape of the shaft body 28 may be circular, oval or polygonal, however, a polygon (for example, triangle 32) shown in FIGS. 10A and 10B is preferable because an accuracy in assembling can be improved without rotation around a shaft. Further, a quadrangular plate body 33 which is capable of readily increasing a sectional area as shown in FIGS. 11A and 11B is most preferable.

Also, in the case of using a quadrangular plate body 33, hole portions 34 and 35 may be in the form of slits such that they extend over the whole length of the support members 29 and 30. With this structure, the plate bodies 33 are more readily built into the support members 29 and 30.

It should be noted that the sectional shape of the plate body 33 need not be identical along the longitudinal direction as a whole, and may be tapered or of a discontinuous shape.

Also, the modification of the structure is permitted, for example, such that screw thread is formed on the shaft bodies 28 or organic resin is made to flow into holes 26 and 27 instead of the shaft bodies 28 and then solidified.

The holes 26 and 27 penetrated by the shaft bodies 28 are limited to a singular number but may be plural as shown in FIGS. 13A and 13B. With this structure, the strength and durability of the joint portion of the flat base body 2 are improved.

Also, it is not always necessary that the shaft bodies 28 penetrate both the support members 23 and 24, and as shown in FIGS. 14A and 14B, the shaft bodies 28 that penetrate the support member 23 are allowed to pass through both ends of the support member 24 so that the respective members are fixed.

Furthermore, the holes 26 and 27 are defined in a direction transverse to a direction along which the flat base body 2 is protruded. However, in the case of using the box-type support members 29 and 30, the holes 26 and 27 may be defined in a direction identical with a direction along which the flat base body is protruded as shown in FIGS. 15A and 15B.

Also, as shown in FIG. 16C, the shaft bodies 28 are inserted into the support member under the condition where an angle θ with respect to a direction of repulsion of the O-ring satisfies 0°<θ<90°, with the result that the coupling of the support members with each other becomes firm.

It should be noted that in order to improve the gas and/or liquid-tightness of the O-ring sealing portion, an elastic member 36 such as a plate spring, a rubber sponge or a spring washer can be inserted between the flat base body 2 and the support member 24.

The shape of the support member, the shape of the shaft body, the insert direction of the shaft body and the use of the elastic member can be appropriately selected in combination. Table 1 exhibits its combination example and corresponding figure No.

combination so that a space is formed in the upper portion of the piezoelectric element on the tip of the sensor device, thereby holding the piezoelectric element portion gas-tightly and/or liquid-tightly with respect to the fluid to be measured. Also, the coating material such as glass or ceramic is heated, and a part of the electrode terminal on the piezoelectric element side which will be coated is coated with the heated coating material simultaneously when a part of the electrode terminal is exposed. Then, the sealing member is held between the surface of the coating material such as glass or ceramic in the periphery of the above exposed electrode terminal and the surface of the presser plate, to thereby hold the electrode terminal gas-tightly and/or liquid-tightly with respect to the fluid to be measured.

Hereinafter, examples of the present invention will be described in more detail, but the present invention is not limited to or by those examples.

TABLE 1

Figure 6:
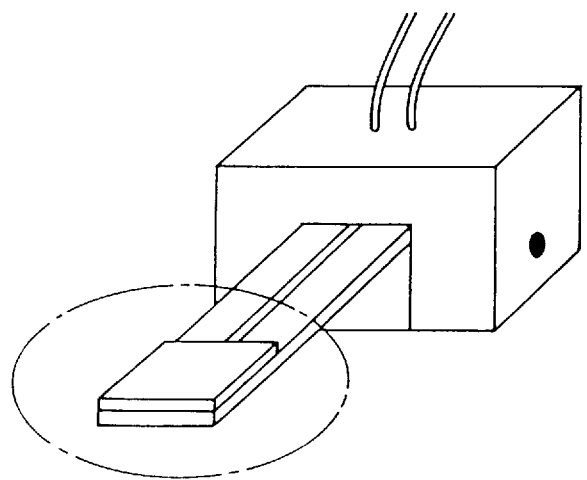
Figure 6:
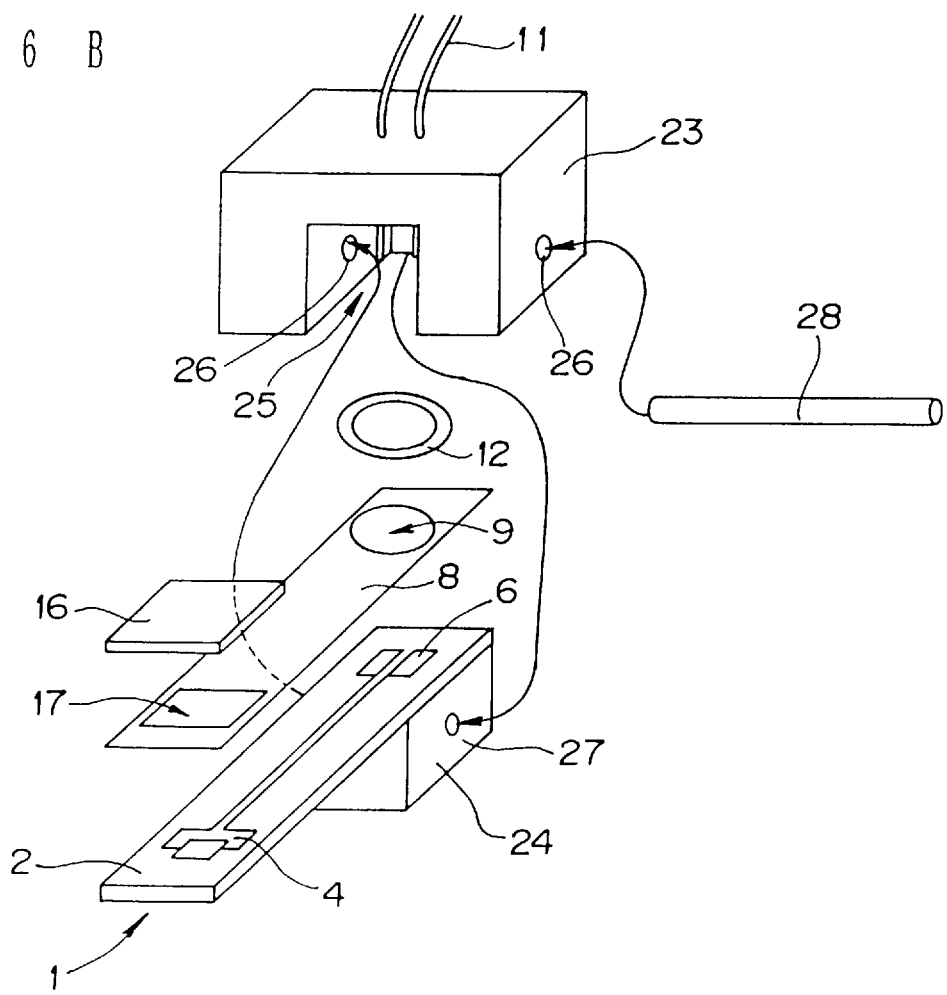
Figure 10:
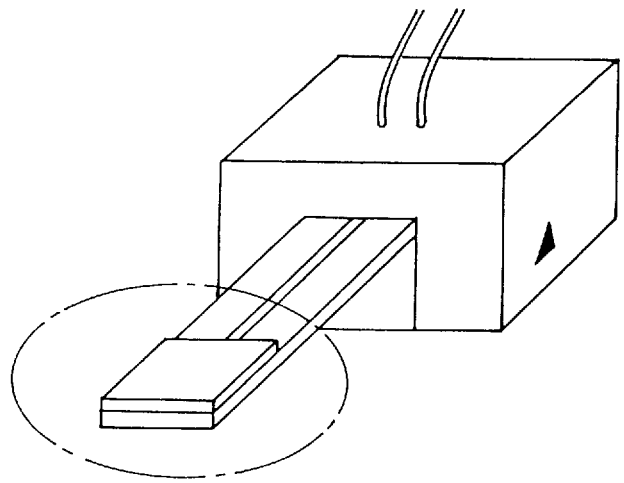
Figure 10:
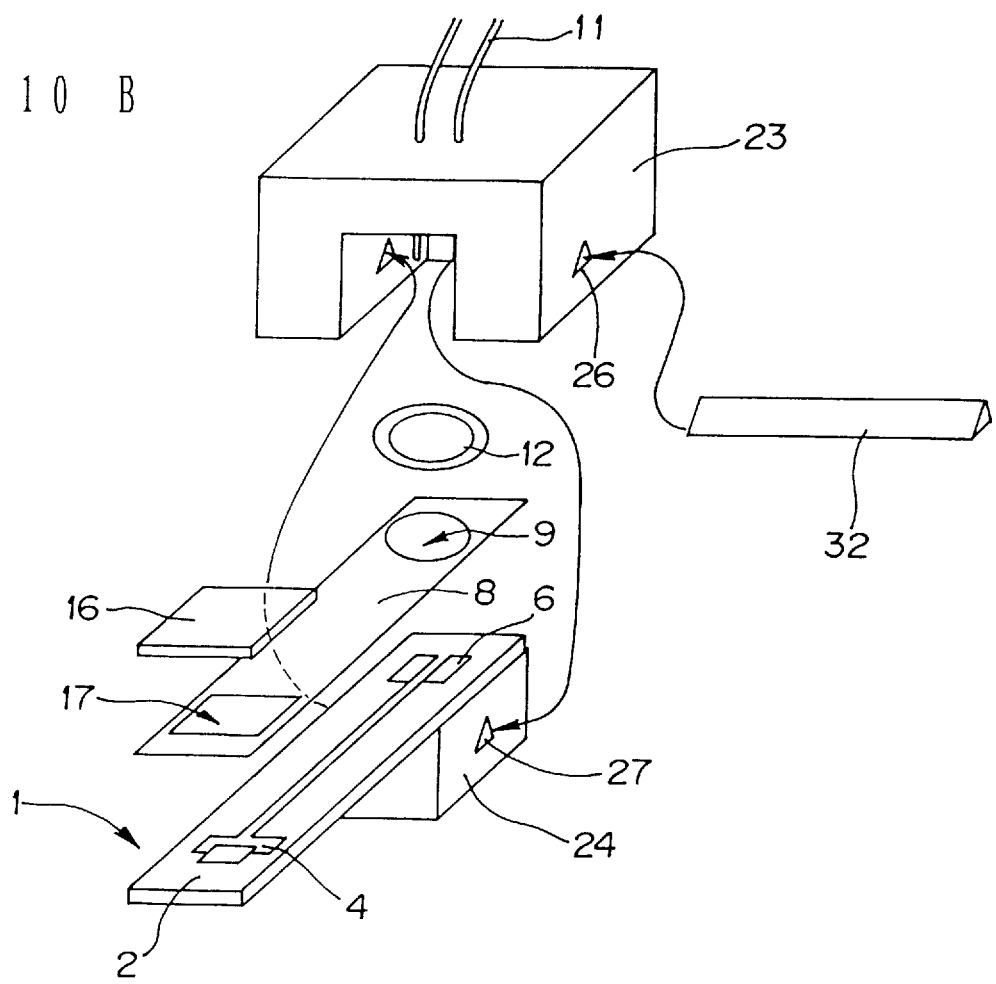
Figure 11:
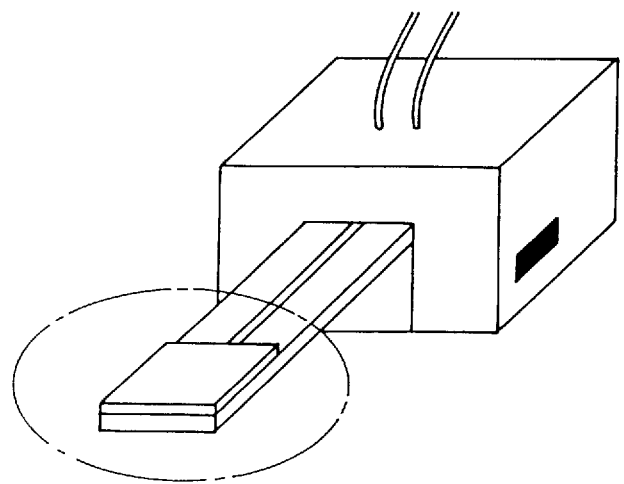
Figure 11:
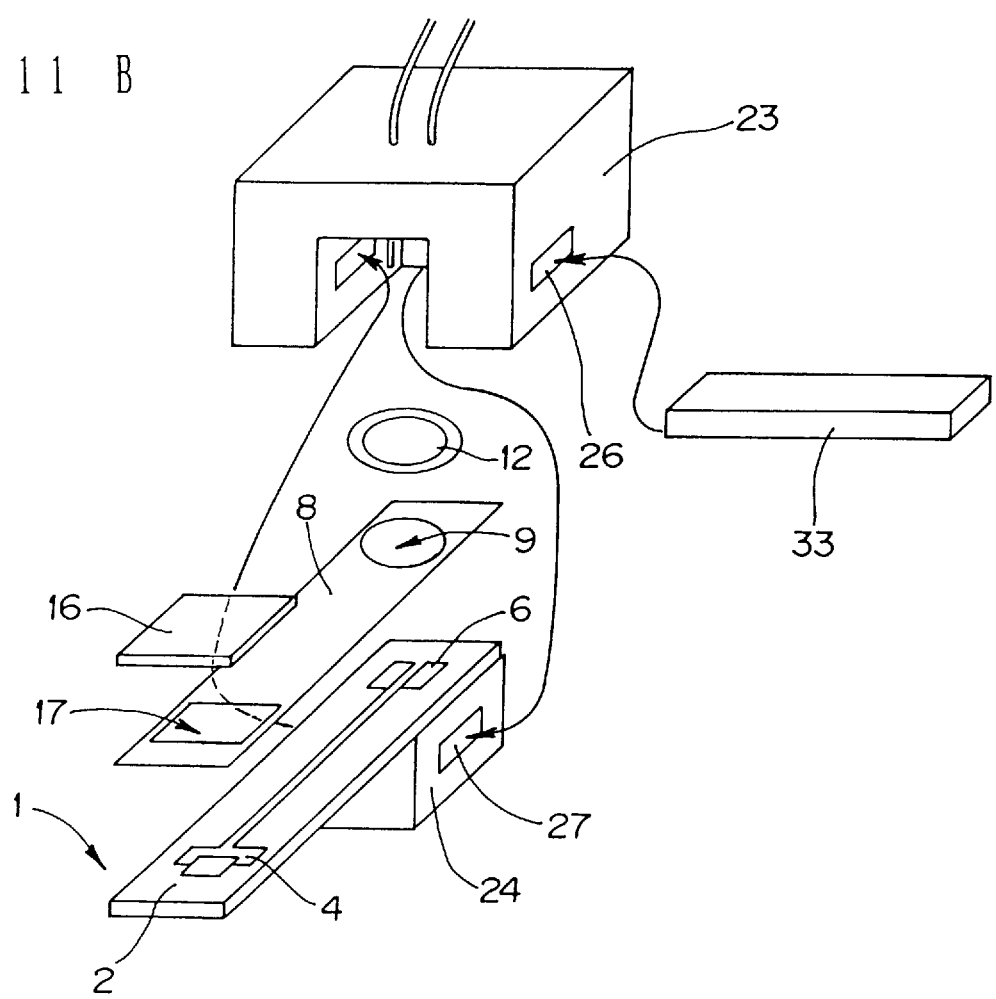
Figure 12A:
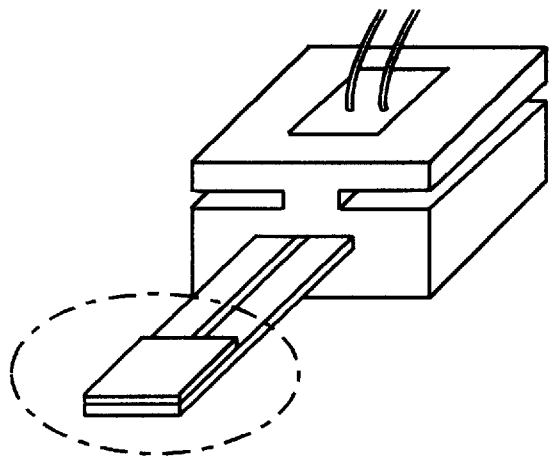
Figure 12B:
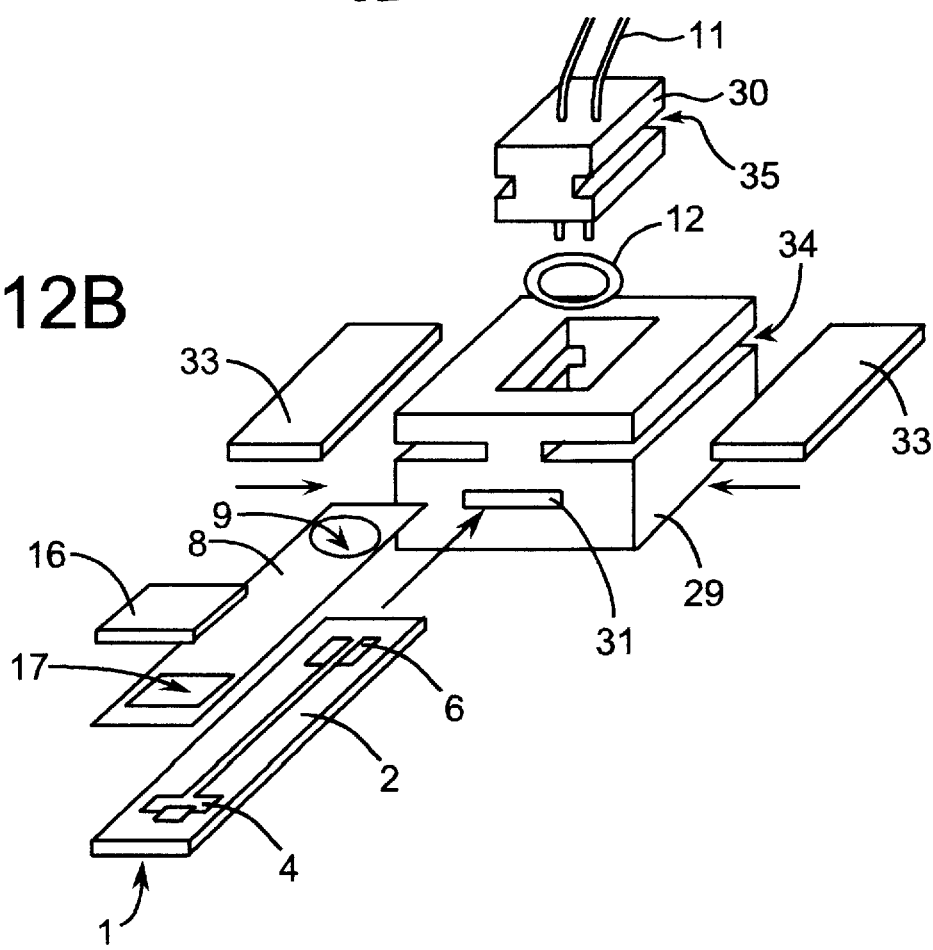
Figure 13:
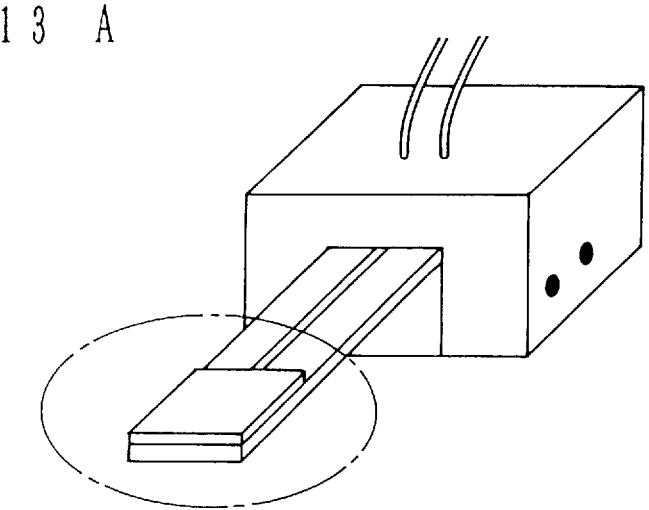
Figure 13:
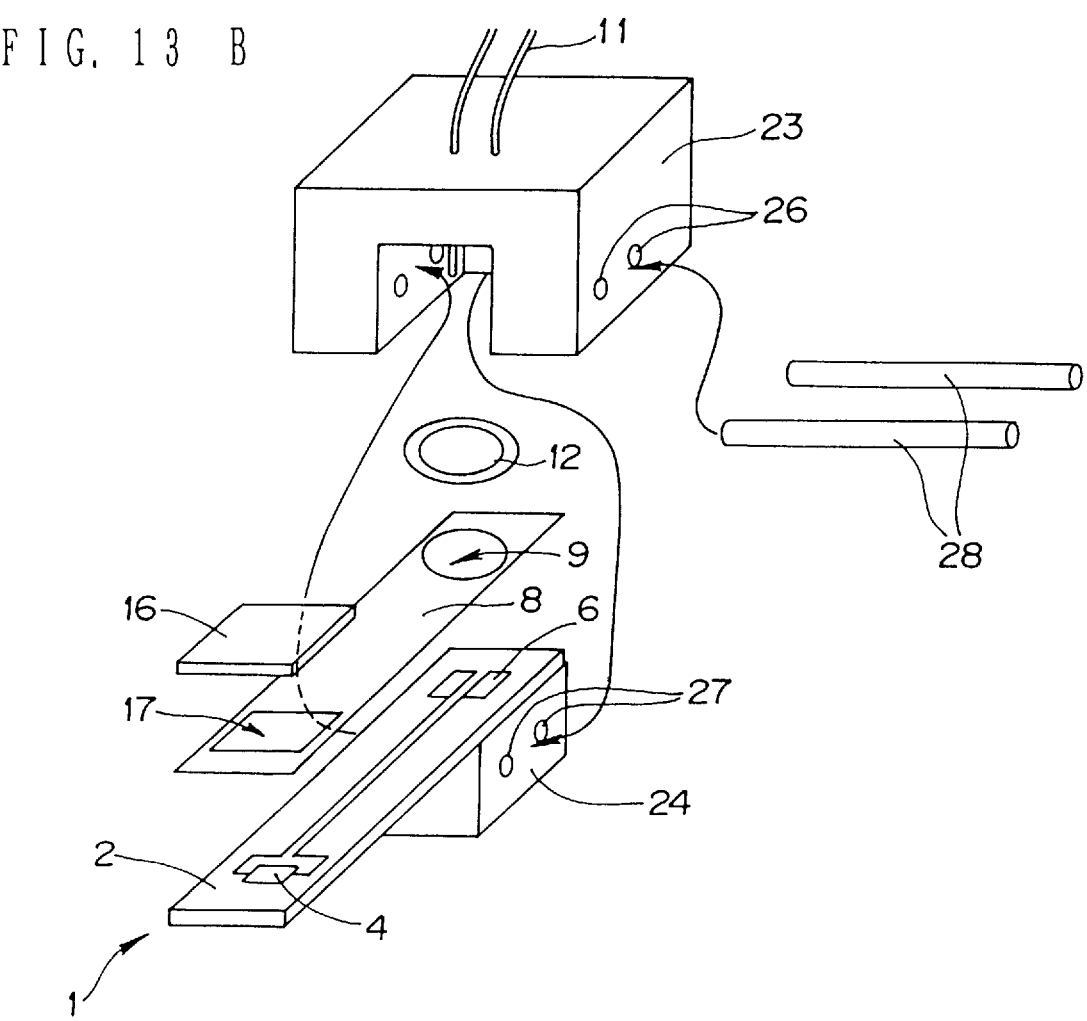
Figure 14:
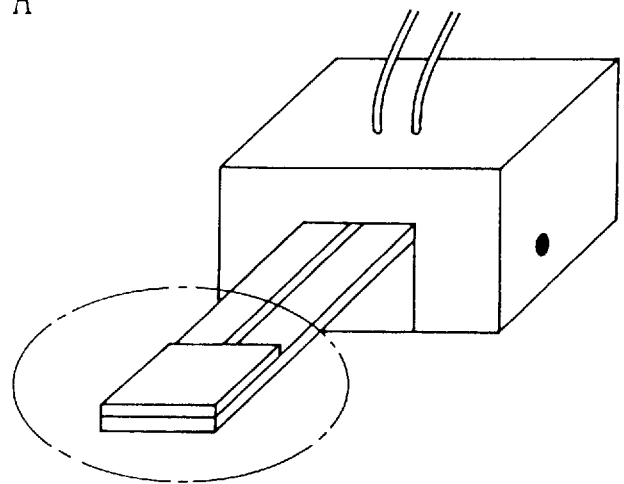
Figure 14:
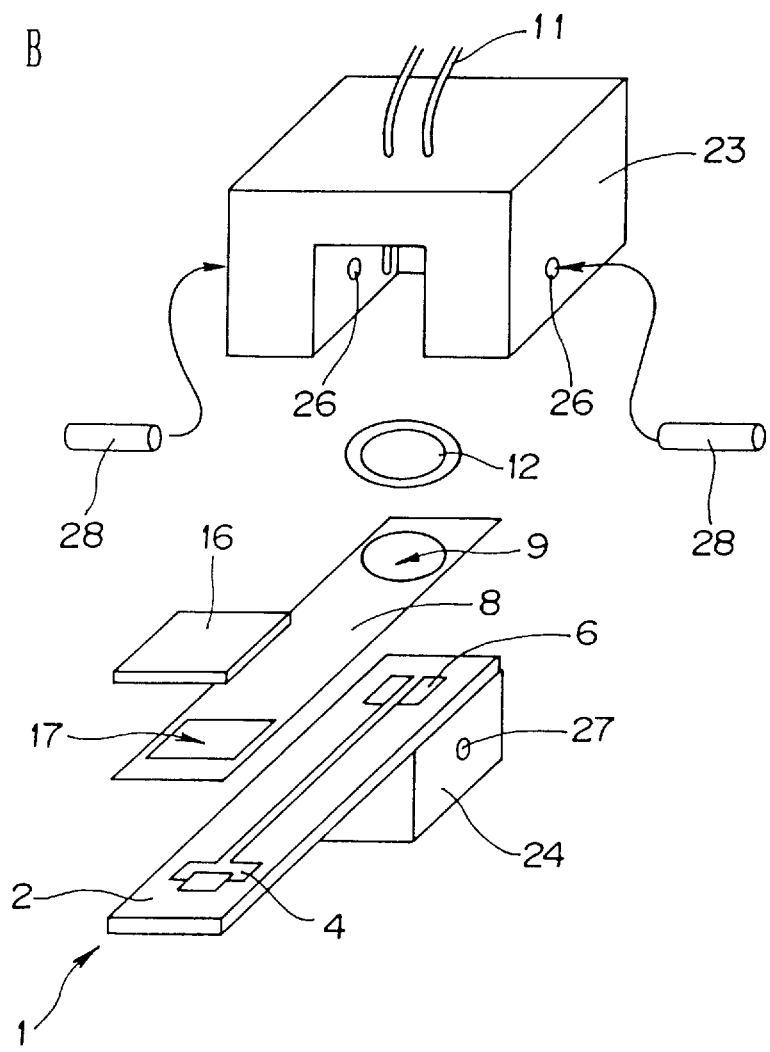
Figure 15:
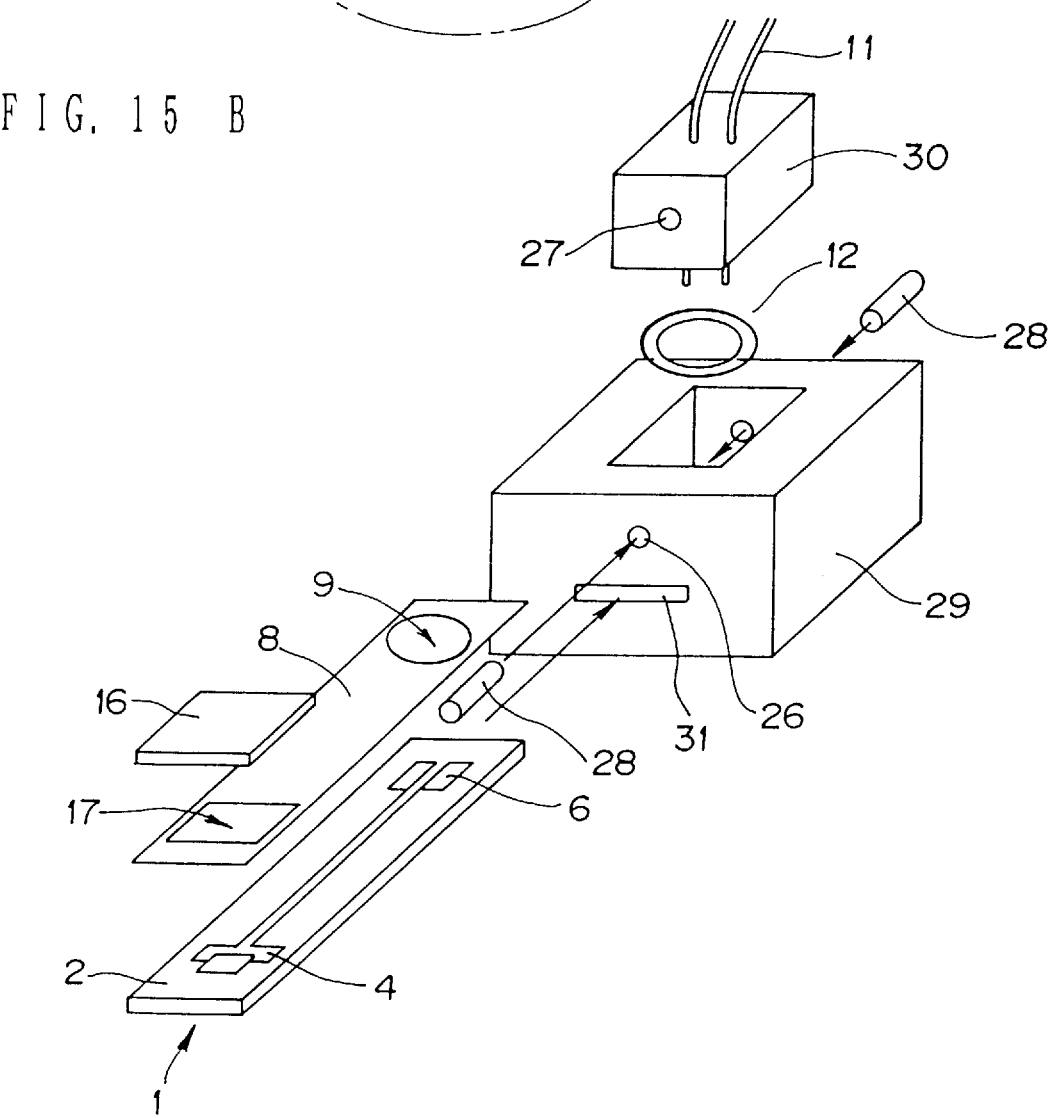
Figure 17A:
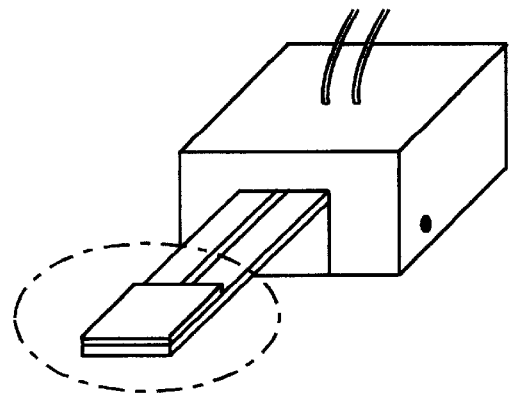
Figure 17B:
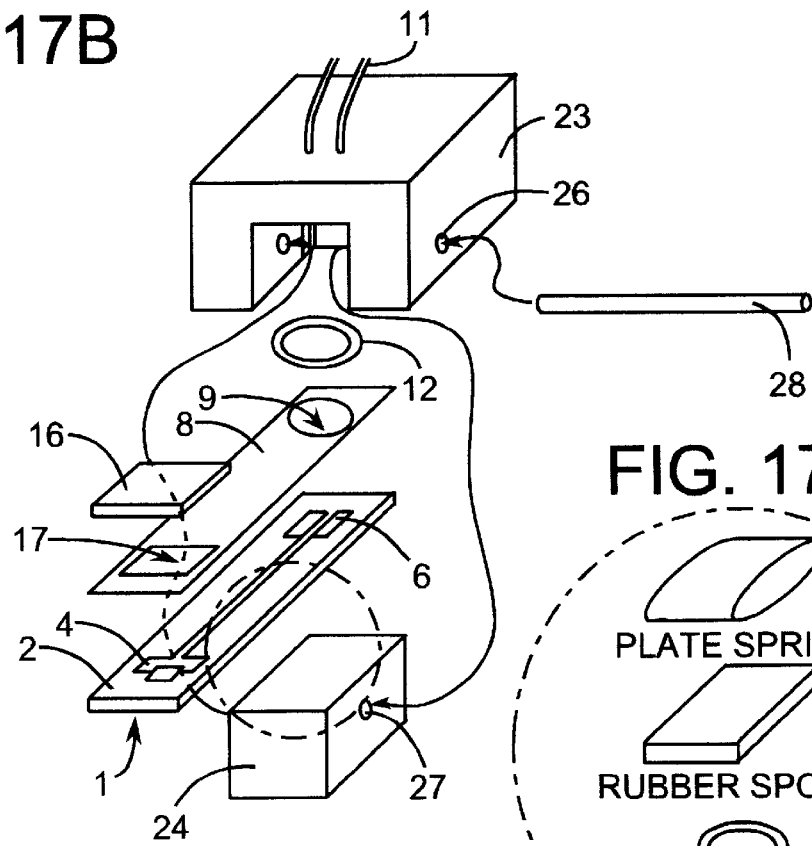
Figure 17C:
Figure 18A:
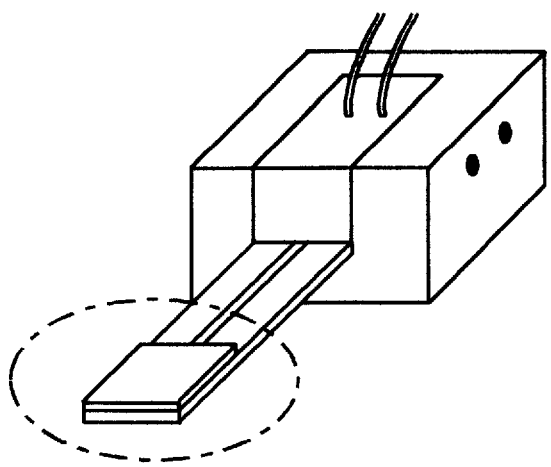
Figure 18B:
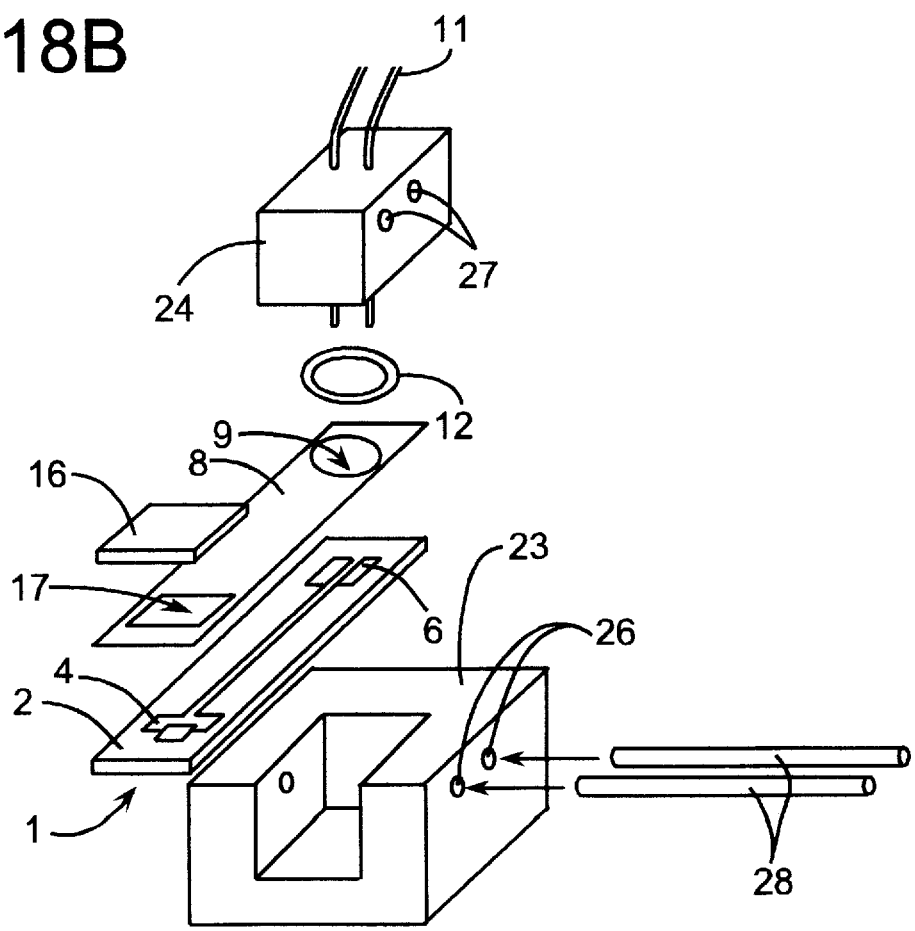
Figure 19A:
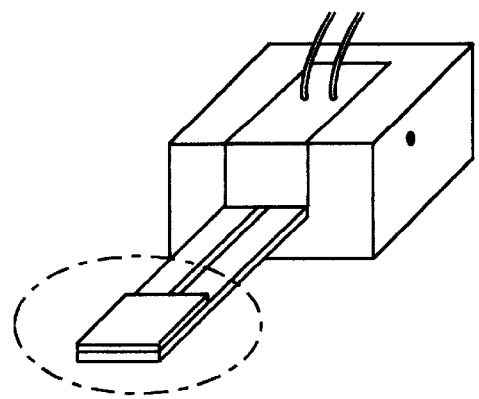
Figure 19B:
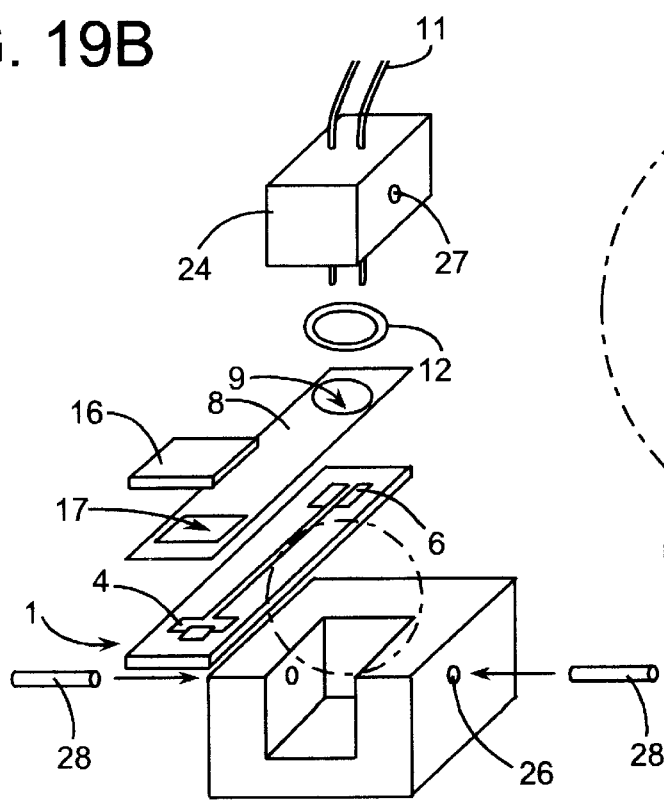
Figure 19C:
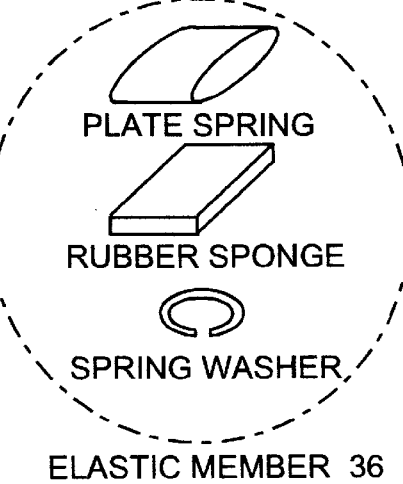
Figure 20:
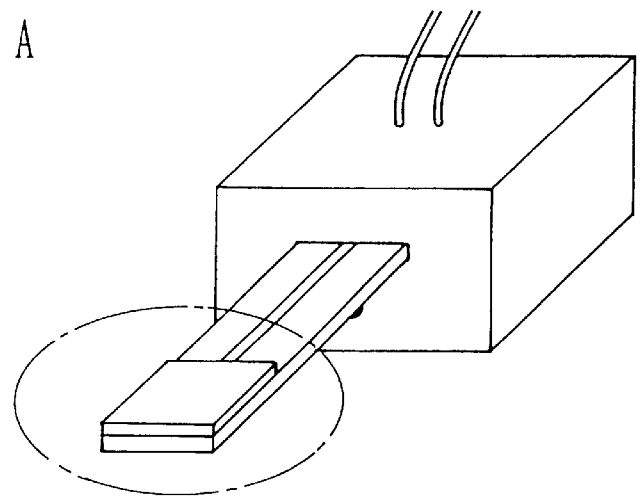
Figure 20:
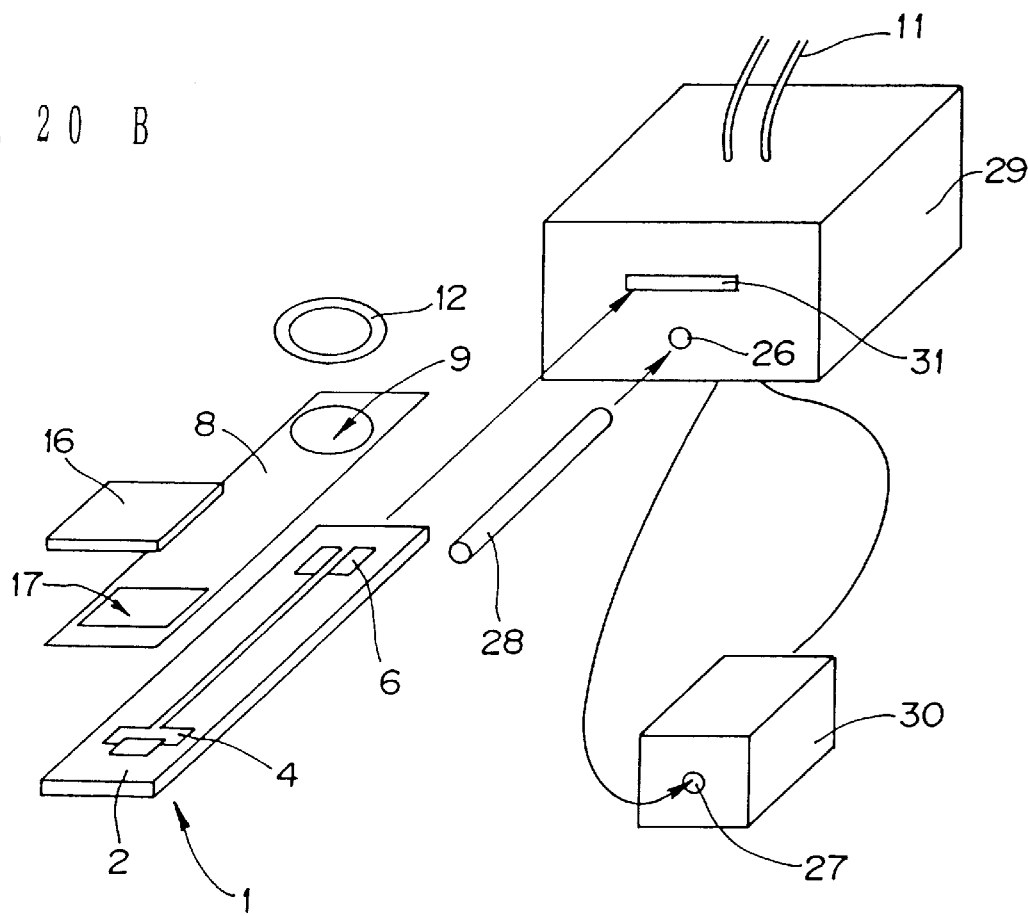
Figure 21A:
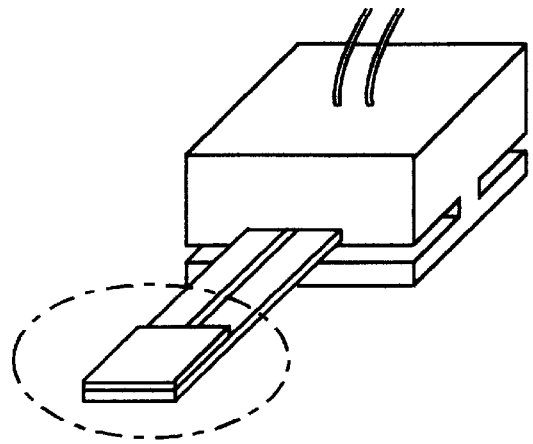
Figure 21B:
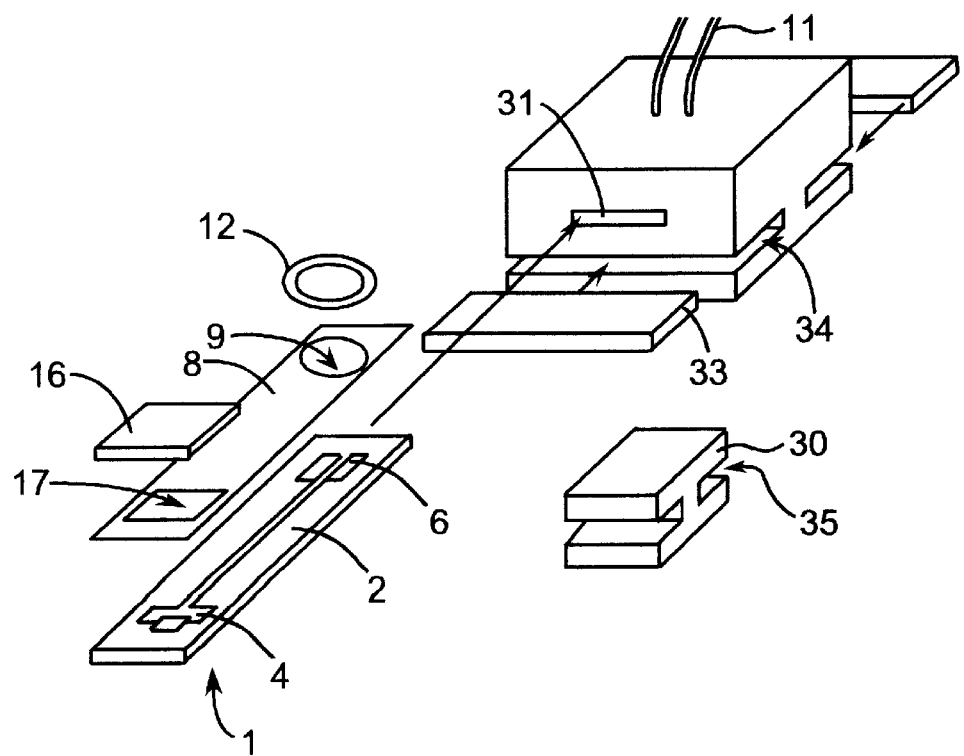
Figure 22A:
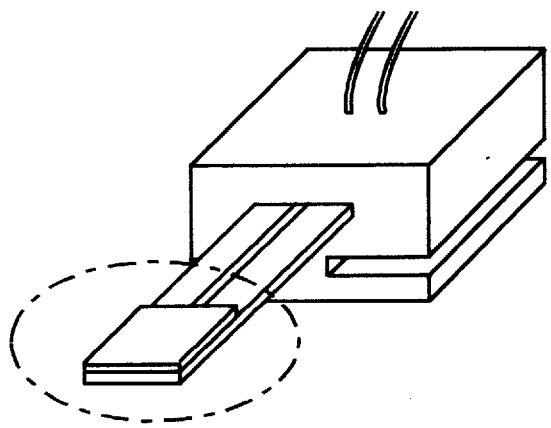
Figure 22B:
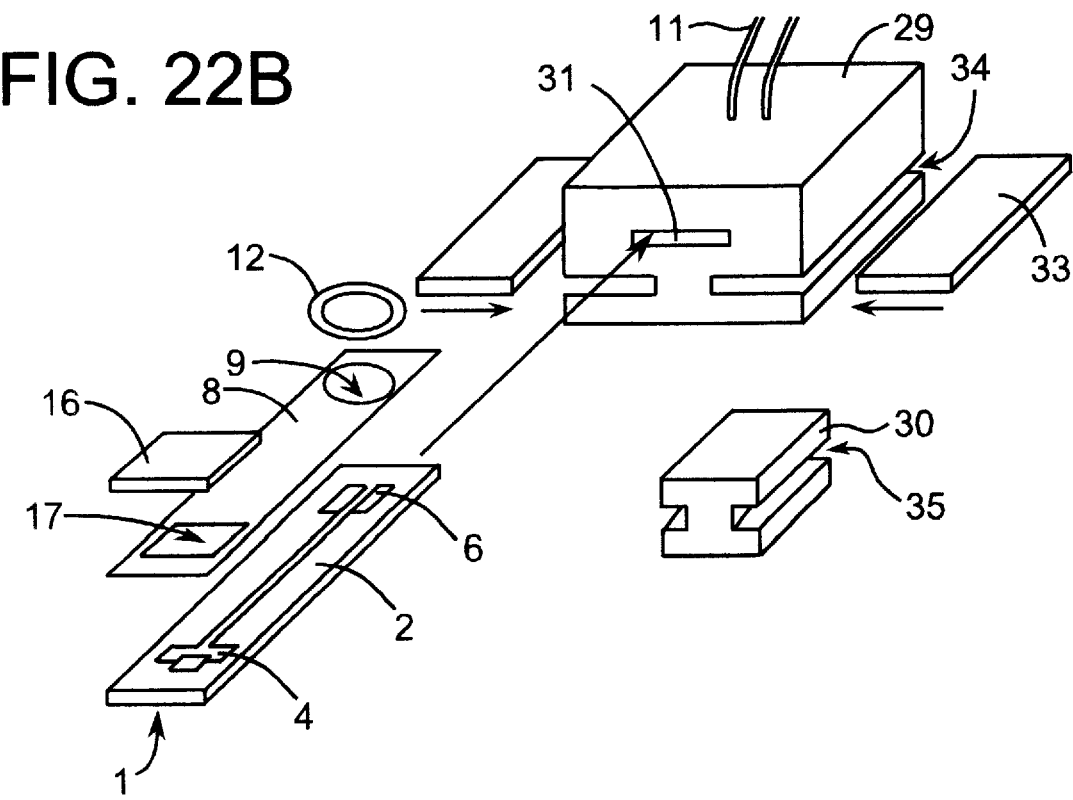
Figure 23A:
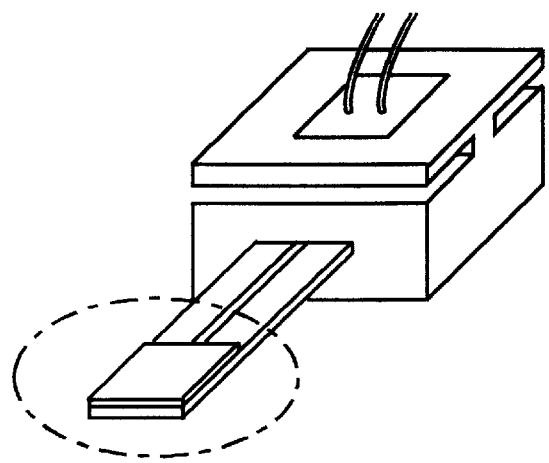
Figure 23B:
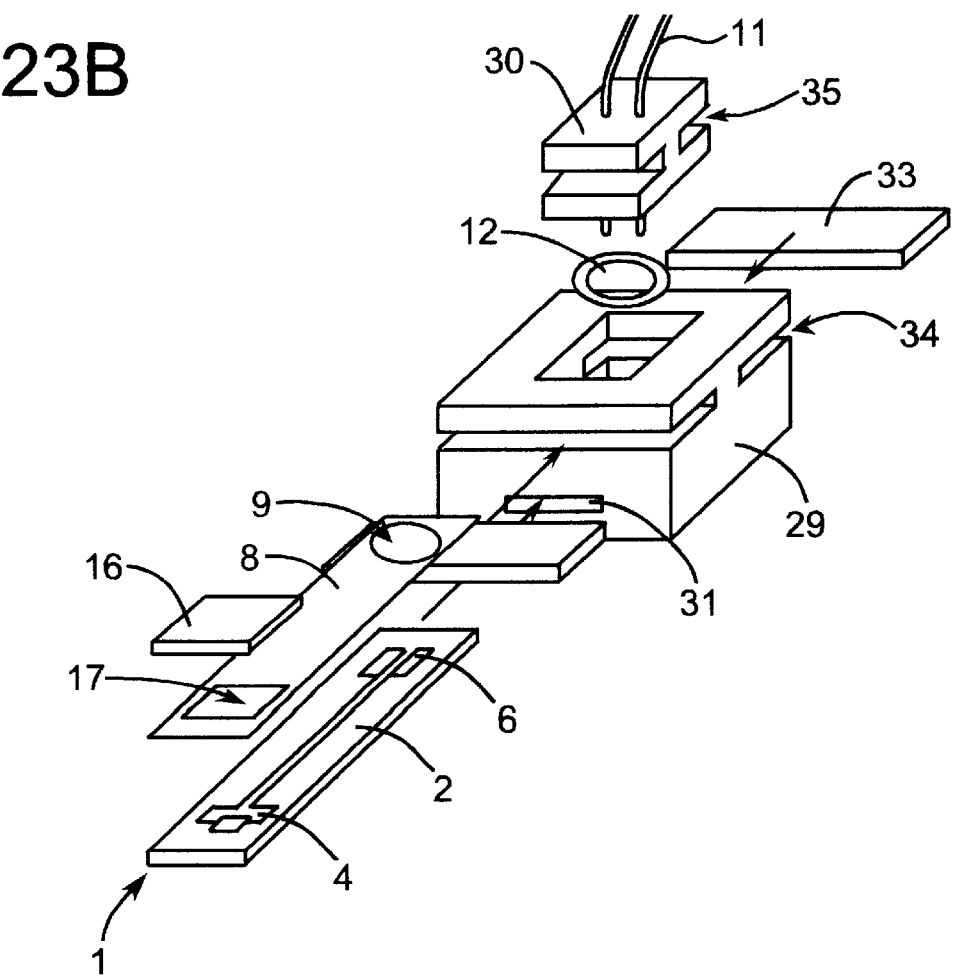
Figure 24A:
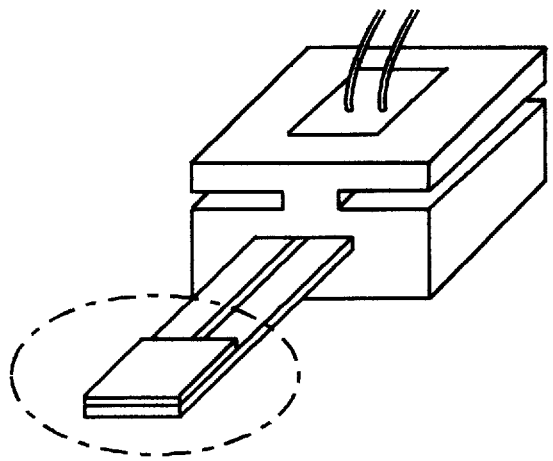
Figure 24B:
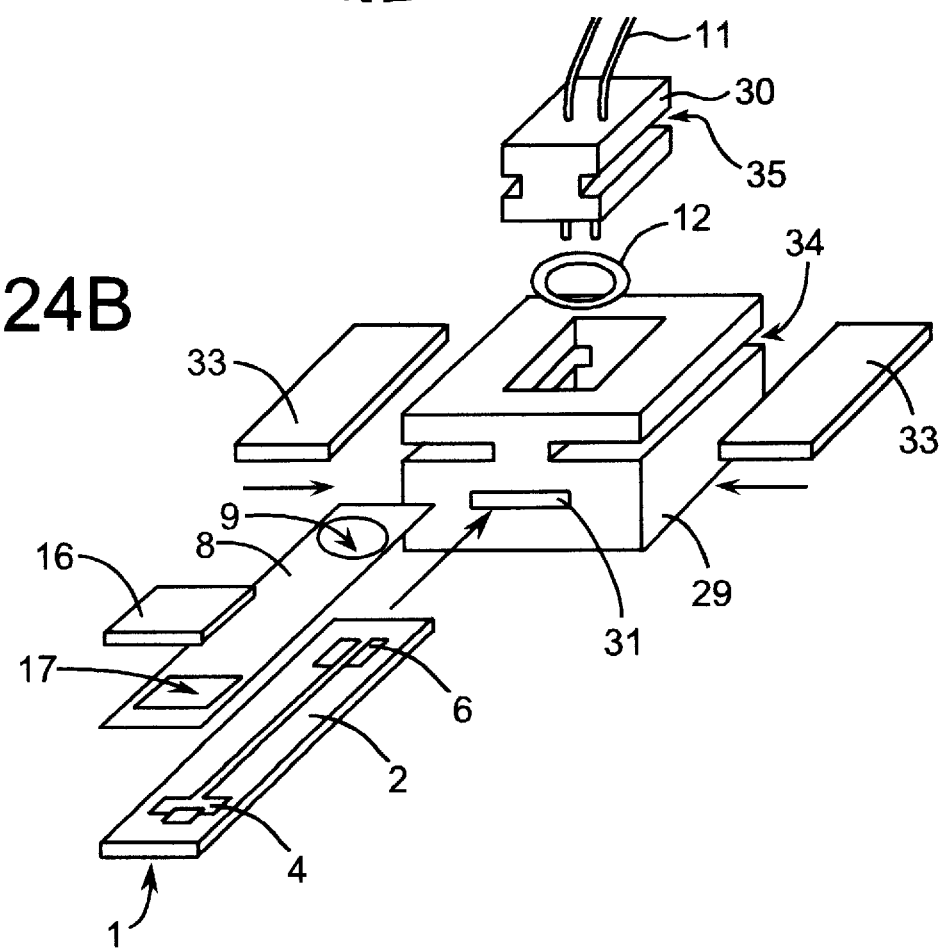
Figure 25:
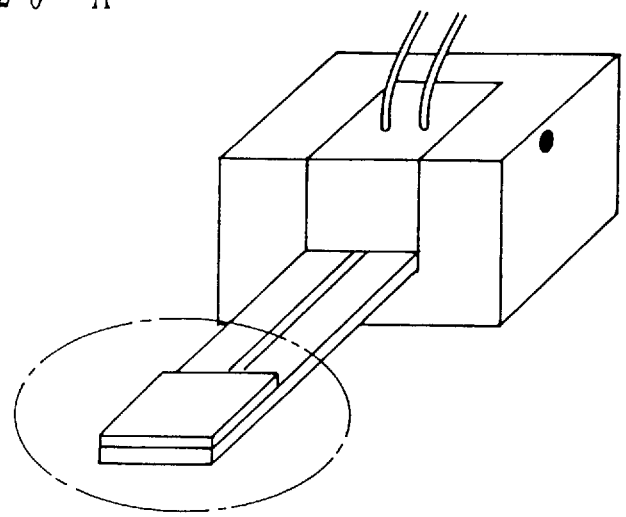
Figure 25:
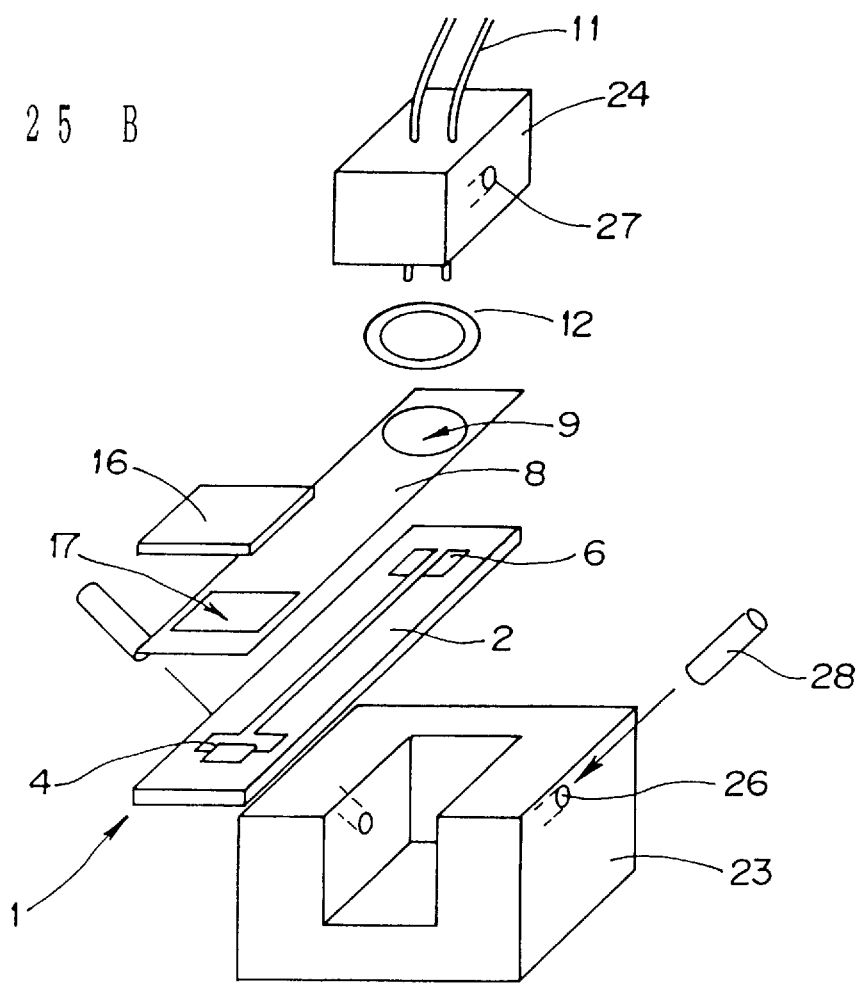
Figure 26A:
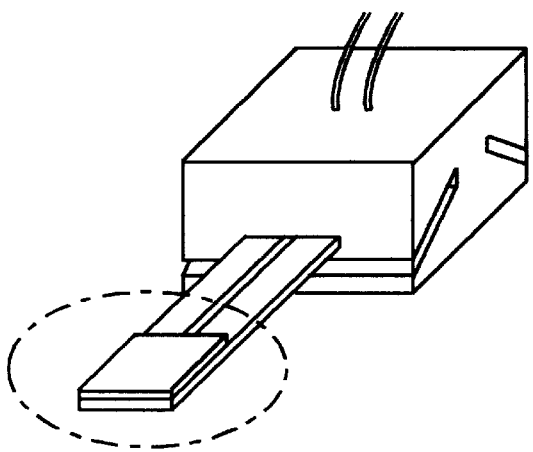
Figure 26B:
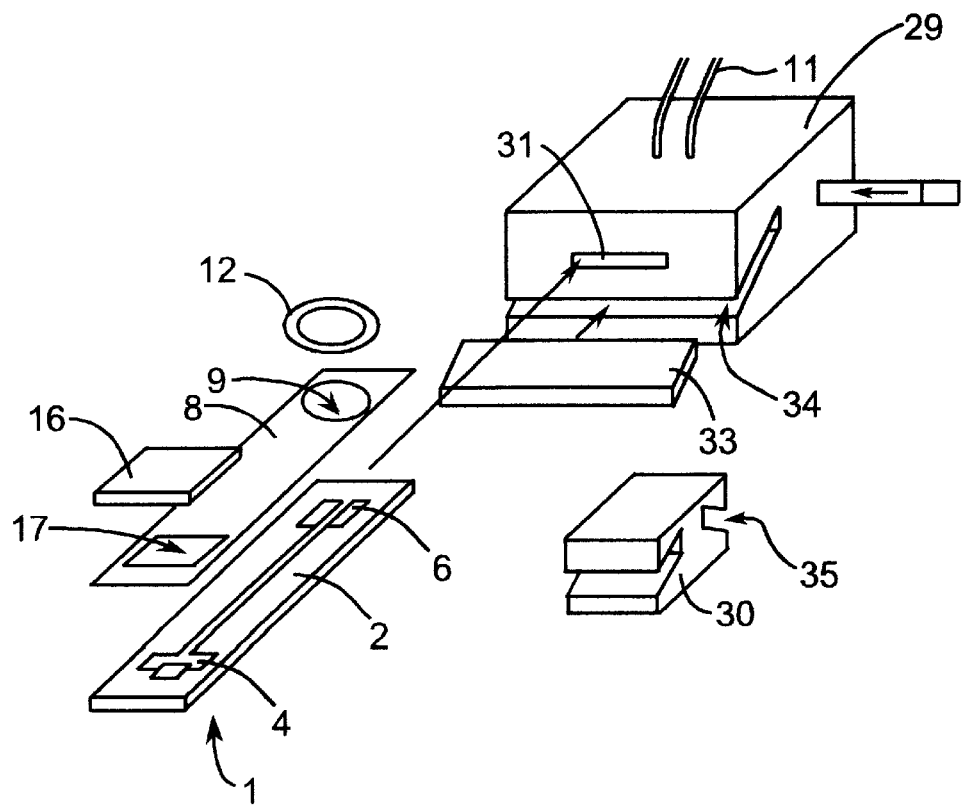
Figure 27A:
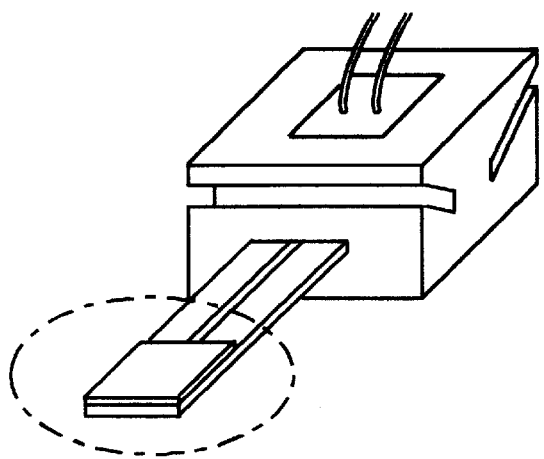
Figure 27B:
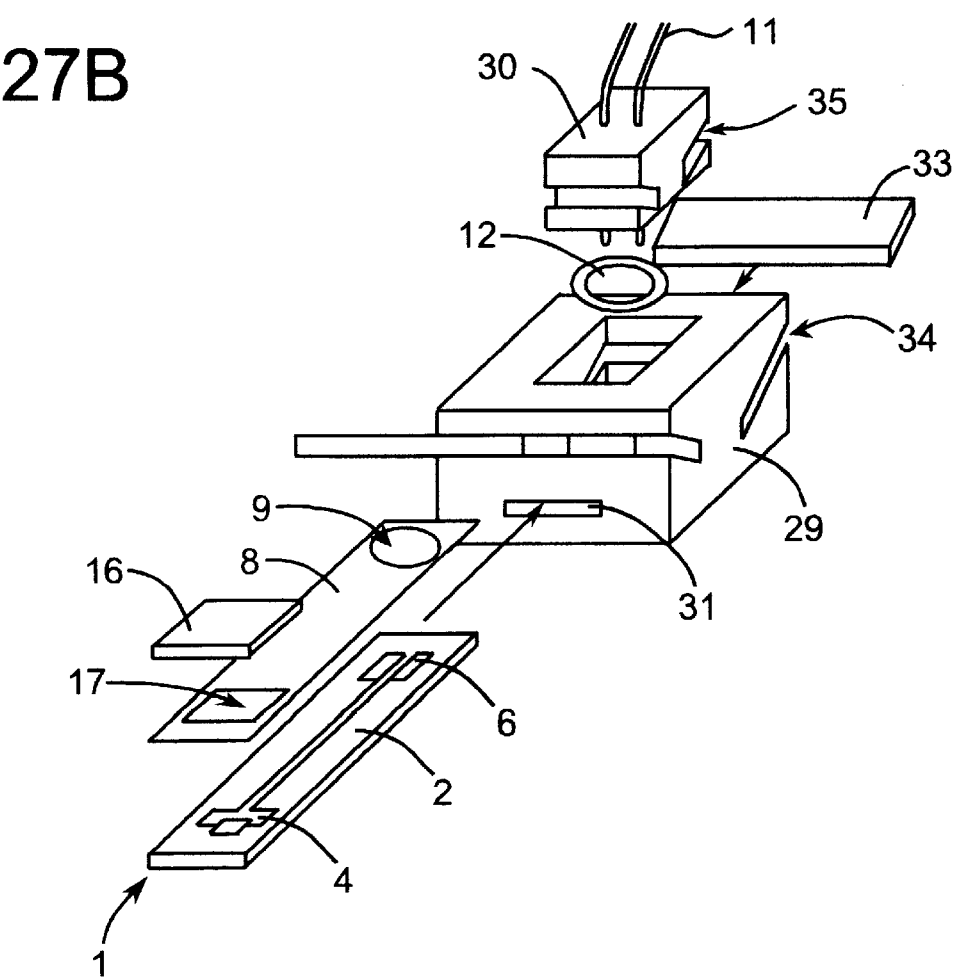

| | support member | | shaft body | | | | | |
|---|---|---|---|---|---|---|---|---|
| No. | shape | upside down arrangement | shape | the number of shaft bodies | penetration, non-penetration | insertion direction of shaft body | auxiliary means | corresponding drawings |
| 1 | standard type | | circular | 1 | penetration | transverse direction | | FIG. 6 |
| 2 | standard type | | circular | 2 | penetration | transverse direction | | FIG. 13 |
| 3 | standard type | | quadrangular plate | 1 | penetration | transverse direction | | FIG. 11 |
| 4 | standard type | upside down | triangular | 1 | penetration | transverse direction | | FIG. 10 |
| 5 | standard type | upside down | circular | 1 + 1 | non-penetration | transverse direction | | FIG. 14 |
| 6 | standard type | | circular | 2 | penetration | transverse direction | | FIG. 18 |
| 7 | standard type | upside down | circular | 1 | penetration | transverse direction | | FIG. 17 |
| 8 | standard type | | circular | 1 + 1 | non-penetration | transverse direction | use | FIG. 19 |
| 9 | box type | upside down | circular | 1 | penetration | the same direction | use | FIG. 20 |
| 10 | box type | | circular | 1 + 1 | non-penetration | the same direction | | FIG. 15 |
| 11 | box type | | quadrangular plate | 1 + 1 | non-penetration | the same direction | | FIG. 21 |
| 12 | box type | | quadrangular plate | 1 + 1 | non-penetration | transverse direction | | FIG. 22 |
| 13 | box type | upside down | quadrangular plate | 1 + 1 | non-penetration | the same direction | | FIG. 23 |
| 14 | box type | upside down | quadrangular plate | 1 + 1 | non-penetration | transverse direction | | FIG. 24 |
| 15 | standard type | | circular | 1 + 1 | non-penetration | transverse direction | | FIG. 16 |
| 16 | standard type | upside down | circular | 1 + 1 | non-penetration | transverse direction + oblique direction | | FIG. 25 |
| 17 | box type | | quadrangular plate | 1 + 1 | non-penetration | the same direction and oblique direction | | FIG. 26 |
| 18 | box type | upside down | quadrangular plate | 1 + 1 | non-penetration | the same direction and oblique direction | | FIG. 27 |

*The upside down arrangement is directed to an arrangement in which upper and lower support members of the standard type and the box type turn upside down.
**1 + 1 in the number of the shaft bodies is directed to a structure in which two shaft bodies are provide coaxially because the shaft body is of the non-penetration type.
***The transverse direction to and the same direction as the insertion direction of the shaft body are directed to an insertion direction with respect to a protrusion direction of the flat base body. The oblique direction is directed to a direction in which the shaft body is inserted with an angle with respect to the repulsion direction of an O-ring.

The cover 16 is used for protecting the piezoelectric element 3, and not essential and arbitrarily selected. The material of the cover 16 may be selected from any one of metal, synthetic resin, ceramics or the like. However, it is preferably ceramic such as $ZrO_2$ from the viewpoint of corrosion resistance. It should be noted that the coating material 8 made of organic resin or glass is joined between the cover 16 and the flat base body 2 as an adhesive layer, and in the case where the cover 16 and the flat base body 2 in addition to the coating material 8 are made of ceramic, these elements can be integrated by sintering.

With the above structure, in the case of using a fluid of strong acid such as sulfuric acid or strong base such as sodium hydroxide aqueous, the cover 16 allows the piezoelectric element 3 and those liquid to be further isolated from each other.

As a preferred embodiment of the present invention, ceramic such as zirconia or glass is heated singly or in (EXAMPLE 1)

A sensor device 1 which has a tip structure shown in FIG. 2 and an electrode terminal 6 exposed from its surface, and is made of zirconia was fabricated by repeating a print sintering.

A coating material 8 of a shape shown in FIGS. 1A and 1B was printed on the upper portion of the sensor device 1 by glass paste, and a plate 16 made of zirconia was mounted on the upper portion of a hollow-out portion 17, and thereafter they were sintered at 700° C. as a whole, thereby forming a device in which the entire electrode terminal was coated with glass and zirconia except for the rear end portion (the hollow-out portion 9) of the electrode terminal 6.

Subsequently, as shown in FIGS. 1A and 1B, after a presser plate 14a made of vinyl chloride, a sealing member 12 made of butyl rubber and the sensor device 1 were positioned, bolts 20 and nuts 22 made of vinyl chloride were fastened in such a manner that the electrode terminal was held gas-tightly and/or liquid-tightly by the sealing member 12, the pressure plate 14a and the glass surface of the surface of the sensor device 1.

Also, an adhesive made of vinyl chloride was supplied between the pressure plate 14a and a lead wire 11 coated with vinyl chloride, resulting in a structure where the space in the electrode terminal portion was completely gas and/or liquid tightly sealed with respect to the fluid to be measured.

As a result that the entire sensor thus structured was submerged in sulfuric acid aqueous of 50% at 60° C. for three months, and its gas-tightness and/or liquid-tightness was measured, the submergence of sulfuric acid into the sensor was not recognized at all.

(EXAMPLE 2)

Through the same method as that in Example 1, a device in which the entire electrode terminal was coated with glass and zirconia was formed.

Subsequently, as shown in FIGS. 11A and 11B, after support members 23 and 24, a sealing member 12 made of butyl rubber and the sensor device 1 were positioned, a quadrangular plate shaft body 33 was inserted into the support members 23 and 24 in such a manner that the electrode terminal was held gas-tightly and/or liquid-tightly by the sealing member 12, the support plates 23, 24 and the glass surface on the surface of the sensor device 1.

Also, an adhesive made of vinyl chloride was supplied between the support plate 23, 24 and a lead wire 11 coated with vinyl chloride, resulting in a structure where the space in the electrode terminal portion was completely gas-tightly and/or liquid-tightly sealed with respect to the fluid to be measured.

As a result that the entire sensor thus structured was submerged in sulfuric acid aqueous of 50% at 60° C. for three months, and its gas-tightness and/or liquid-tightness was measured, the submergence of sulfuric acid into the sensor was not recognized at all.

As was described above, according to the fluid sensor of the present invention, the electrode terminal portion for extracting a signal from the sensor device to the exterior can be readily and firmly held gas-tightly and/or liquid-tightly with respect to the fluid. Hence, the present invention can be preferably applied particularly to a fluid sensor that actuates in a corrosive fluid such as sulfuric acid in a lead storage battery, in a polar solvent, or in a solution using the polar solvent.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fluid sensor, comprising:

a base body having a vibrating portion;

a piezoelectric element which is fixed onto one surface of said vibrating portion and has a piezoelectric film and at least a pair of electrodes which are disposed in contact with said piezoelectric film;

an electrode terminal which is disposed on the surface of said base body and electrically connected to said pair of electrodes;

a coating material which is disposed on the surface of said base body in the periphery of said electrode terminal; a presser plate; and a sealing member which is held between said base body and said presser plate and formed so as to surround said electrode terminal where said pressure plate applies pressure to said sealing member against said coating material;

wherein said electrode terminal is held gas-tightly and/or liquid-tightly with respect to a fluid to be measured by holding said sealing member between said coating material and said presser plate.

2. A fluid sensor as claimed in claim 1, further comprising a lead wire that penetrates said presser plate; and an electrode connection member disposed on a top of said lead wire;

wherein said electrode connection member and said electrode terminal are in contact with each other.

3. A fluid sensor as claimed in claim 1, wherein said base body is in the form of a flat plate comprising ceramic material.

4. A fluid sensor as claimed in claim 1, wherein said sealing member is in the form of an O-ring.

5. a fluid sensor, comprising:

a base body having a vibrating portion;

a piezoelectric element which is fixed onto one surface of said vibrating portion and has a piezoelectric film and at least a pair of electrodes which are disposed in contact with said piezoelectric film;

an electrode terminal which is disposed on the surface of said base body and electrically connected to said pair of electrodes;

a coating material disposed on the surface of said base body;

a presser plate; and a sealing member which is held between said coating material and at least said pressure plate where said pressure plate applies pressure to said sealing member against said coating material, wherein said electrode terminal is held gas-tightly and/or liquid-tightly with respect to a fluid to be measured by holding said sealing member between said coating material and said presser plate.

* * * * *